(12) United States Patent
Lee et al.

(10) Patent No.: US 10,640,774 B2
(45) Date of Patent: May 5, 2020

(54) RECOMBINANT MICROORGANISM HAVING ABILITY TO PRODUCE POLY(LACTATE-COGLYCOLATE) OR COPOLYMER THEREOF FROM XYLOSE AND METHOD FOR PREPARING POLY(LACTATE-COGLYCOLATE) OR COPOLYMER THEREOF BY USING SAME

(71) Applicant: KOREA ADVANCED INSTITUTE OF SCIENCE AND TECHNOLOGY, Daejeon (KR)

(72) Inventors: Sang Yup Lee, Daejeon (KR); So Young Choi, Daejeon (KR); Si Jae Park, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 16/071,680

(22) PCT Filed: Dec. 13, 2016

(86) PCT No.: PCT/KR2016/014574
§ 371 (c)(1),
(2) Date: Jul. 20, 2018

(87) PCT Pub. No.: WO2017/131342
PCT Pub. Date: Aug. 3, 2017

(65) Prior Publication Data
US 2019/0024093 A1    Jan. 24, 2019

(30) Foreign Application Priority Data
Jan. 28, 2016 (KR) .................. 10-2016-0010549

(51) Int. Cl.
| | | |
|---|---|---|
| C12N 15/52 | (2006.01) | |
| C12N 9/10 | (2006.01) | |
| C12N 15/63 | (2006.01) | |
| C12N 15/70 | (2006.01) | |
| C12N 9/02 | (2006.01) | |
| C12N 9/04 | (2006.01) | |
| C12N 1/20 | (2006.01) | |
| C12P 7/40 | (2006.01) | |
| C12N 9/18 | (2006.01) | |

(52) U.S. Cl.
CPC .............. *C12N 15/52* (2013.01); *C12N 1/20* (2013.01); *C12N 9/001* (2013.01); *C12N 9/0006* (2013.01); *C12N 9/0008* (2013.01); *C12N 9/10* (2013.01); *C12N 9/104* (2013.01); *C12N 9/18* (2013.01); *C12N 15/63* (2013.01); *C12N 15/70* (2013.01); *C12P 7/40* (2013.01); *C12Y 101/01002* (2013.01); *C12Y 101/01028* (2013.01); *C12Y 101/01113* (2013.01); *C12Y 102/03003* (2013.01); *C12Y 103/01006* (2013.01); *C12Y 197/01004* (2013.01); *C12Y 203/01176* (2013.01); *C12Y 301/01068* (2013.01)

(58) Field of Classification Search
CPC .... C12Y 101/01113; C12Y 102/03003; C12Y 101/01002; C12Y 301/01068; C12Y 203/01176; C12Y 197/01004; C12Y 103/01006; C12Y 101/01028; C12N 15/70; C12N 9/001; C12N 9/0008; C12N 9/0006; C12N 1/20; C12N 9/104; C12N 9/10; C12N 9/18; C12N 15/52; C12N 15/63; C12P 7/40
See application file for complete search history.

(56) References Cited

U.S. PATENT DOCUMENTS

| | | | |
|---|---|---|---|
| 6,143,952 A | 11/2000 | Srienc et al. | |
| 8,349,587 B2 * | 1/2013 | Fischer | ...................... C12P 5/00 435/41 |
| 8,883,463 B2 | 11/2014 | Lee et al. | |
| 9,034,615 B2 * | 5/2015 | Soucaille | .................. C12P 7/42 435/146 |
| 2013/0078673 A1 | 3/2013 | Lee et al. | |
| 2014/0030775 A1 | 1/2014 | Lee et al. | |
| 2015/0337342 A1 | 11/2015 | Zhang et al. | |

FOREIGN PATENT DOCUMENTS

| | | |
|---|---|---|
| JP | 2001516574 A | 10/2001 |
| JP | 2012152171 A | 8/2012 |
| JP | 2014012822 A | 1/2014 |
| JP | 2014030376 A | 2/2014 |

(Continued)

OTHER PUBLICATIONS

Broun et al., Catalytic plasticity of fatty acid modification enzymes underlying chemical diversity of plant lipids. Science, 1998, vol. 282: 1315-1317. (Year: 1998).*

(Continued)

*Primary Examiner* — Ganapathirama Raghu
(74) *Attorney, Agent, or Firm* — Hultquist, PLLC; Steven J. Hultquist

(57) ABSTRACT

The present invention relates to a recombinant microorganism having the ability to produce poly(lactate-co-glycolate) and its copolymers from xylose, and more particularly to a recombinant microorganism having the ability to produce poly(lactate-co-glycolate) and its copolymers without having to supply a glycolate precursor from an external source, and a method of producing a poly(lactate-co-glycolate) copolymers using the same.

14 Claims, 8 Drawing Sheets
(8 of 8 Drawing Sheet(s) Filed in Color)
Specification includes a Sequence Listing.

(56) References Cited

FOREIGN PATENT DOCUMENTS

| KR | 10-2009-0017252 A | 2/2009 | | |
|---|---|---|---|---|
| KR | 10-2010-0099534 A | 9/2010 | | |
| KR | 2010-0099534 | * | 9/2010 | ............ C12N 15/70 |
| KR | 10-2010-0111766 A | 10/2010 | | |
| KR | WO2011074842 | * | 6/2011 | ............ C12N 15/54 |
| KR | 10-2012-0103996 A | 9/2012 | | |
| KR | 10-1211767 B1 | 12/2012 | | |
| WO | WO9854329 A1 | 12/1998 | | |
| WO | WO9961624 A2 | 12/1999 | | |
| WO | WO0155436 A1 | 8/2001 | | |
| WO | 2013069634 A1 | 5/2013 | | |

OTHER PUBLICATIONS

Devos et al., Practical limits of function prediction. Proteins: Structure, Function, and Genetics. 2000, vol. 41: 98-107. (Year: 2000).*

Seffernick et al., Melamine deaminase and Atrazine chlorohydrolase: 98 percent identical but functionally different. J. Bacteriol., 2001, vol. 183 (8): 2405-2410. (Year: 2001).*

Stephens et al., Genetic analysis of a novel pathway for D-xylose metabolism in Caulobacter crescentus. J. Bacteriol., 2007, vol. 189 (5): 2181-2185. (Year: 2007).*

Whisstock et al., Prediction of protein function from protein sequence. Q. Rev. Biophysics., 2003, vol. 36 (3): 307-340. (Year: 2003).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

Choi et al., One-step fermentation production of poly(lactate-co-glycolate) from carbohydrates in *Escherichia coli*. Nature Biotechnology, 2016, vol. 34(4): 435-440; additional 2 pages Online methods; and plus additional 35 pages of Supplementary 1 to Supplementary Notes; published online Mar. 7, 2016. (2016).*

Choi, S., et al., "One-Step Fermentative Production of Poly(lactate-co-glycolate) From Carbohydrates in *Escherichia coli*", "Nature Biotechnology", Apr. 2016, pp. 435-440, vol. 34, No. 4.

Jacquel, N., et al., "Isolation and purification of bacterial poly(3-hydroxyalkanoates)", "Biochemical Engineering Journal", 2008, pp. 15-27, vol. 39.

Langenbach, S., et al., "Functional expression of the PHA synthase gene phaC1 from Pseudomonas aeruginosa in *Escherichia coli* results in poly(3-hydroxyalkanoate) synthesis", "FEMS Microbiology Letters", 1997, pp. 303-309, vol. 150.

Qi, Q., et al., "Synthesis of poly(3-hydroxyalkanoates) in *Escherichia coli* expressing the PHA synthase gene phaC2 from Pseudomonas aeruginosa: comparison of PhaC1 and PhaC2", "FEMS Microbiology Letters", 1997, pp. 155-162, vol. 157.

Qi, Q., et al., "Metabolic routing towards polyhydroxyalkanoic acid synthesis in recombinant *Escherichia coli* (fadR): inhibition of fatty acid B-oxidation by acrylic acid", "FEMS Microbiology Letters", 1998, pp. 89-94, vol. 167.

Yang, T., et al., "Biosynthesis of Polylactic Acid and its Copolymers Using Evolved Propionate CoA Transferase and PHA Synthase", "Biotechnology and Bioengineering", Jan. 1, 2010, pp. 150-160, vol. 105, No. 1.

Yang, T., et al., "Tailor-made Type II Pseudomonas PHA Synthases and Their Use for the Biosynthesis of Polylactic Acid and its Copolymer in Recombinant *Escherichia coli*", "Appl Microbiol Biotechnol", 2011, pp. 603-614, vol. 90.

Cam, Y., et al., "Engineering of a Synthetic Metabolic Pathway for the Assimilation of (D)-Xylose into Value-Added Chemicals", "Synthetic Biology", 2016, pp. 607-618, vol. 5, No. 7, Publisher: American Chemical Society.

Li, Z., et al., "Biosynthesis of Poly(glycolate-co-lactate-co-3-hydroxybutyrate) from Glucose by Metabolically Engineered *Escherichia coli*", "Metabolic Engineering", 2016, pp. 18, vol. 35.

Zhou, X., et al., "Hyperproduction of Poly(4-hydroxybutyrate) from Glucose by Recombinant *Escherichia coli*", "Microbial Cell Factories", 2012, pp. 1-8, vol. 11, No. 54.

Cam, Y., et al., "Engineering of a synthetic metabolic pathway for the assimilation of (D)-xylose into value-added chemicals", "ACS Synthetic Biology", 2015, pp. 1-39, Publisher: ACS Paragon Plus Environment.

Choi, J-I, et al., "Production of Ploy (3-hydroxybutyrate) [P(3HB)] with High P(3HB) Content by Recombinant *Escherichia coli* Harboring the Alcaligenes latus P(3HB) Biosynthesis Genes and the *E.coli* fitsZ Gene", "Journal of Microbiology and Biotechnology", 1999, pp. 722-725, vol. 9, No. 6, Publisher: The Korean Society for Applied Microbiology.

Choi, S.Y., et al., "One-step fermentative production of poly (lactate-co-glycolate) from carbohydrates in *Escherichia coil*", "Nature Biotechnology", Apr. 2016, pp. 435-440, vol. 34, No. 4, Publisher: npg, Natura America, Inc.

Choi, S.Y., et al., "One-step fermentative production of poly (lactate-co-glycolate) from carbohydrates in *Escherichia coli*", "Nature Biotechnology", Apr. 2016, Page(s) doi:10.1038/nbt.3485, vol. 34, No. 4, Publisher: npg, Nature America, Inc.

Davis, R., et al., "Biosynthesis of polyhydroxyalkanoates co-polymer in *E. coli* using genes from Pseudomonas and Bacillus", "Antonie van Leeuwenhoek", 2008, pp. 207-216, vol. 94, Publisher: Springer Science+Business Media B.V. 2008.

Lindenkamp, N., et al., "A propionate CoA-transferase of Ralstonia eutropha H16 with broad substrate specificity catalyzing the CoA thioester formation of various carboxylic acids", "Appl Microbiol Biotechnol", 2013, pp. 7699-7709, vol. 97, Publisher: Springer.

Park, S.J., et al., "Metabolic engineering of Ralstonia eutropha for the biosynthesis of 2-hydroxyacid-containing polyhydroxyalkanoates", "Metabolic Engineering", 2013, pp. 20-28, vol. 20, Publisher: Elsevier.

Song, Y., et al., "Engineered Corynebacterium glutamicum as an endotoxin-free platform strain for lactate-based polyester production", "Appl Microbiol Biotechnol", 2012, pp. 1917-1925, vol. 93, Publisher: Springer.

Tran, T., et al., "Lactic Acid Containing Polymers Produced in Engineered Sinorhizobium meliloti and Pseudomonas putida", "bioRxiv", May 31, 2019, Page(s) doi: http://dx.doi.org/10.1101/656926.

Weimberg, R., "Pentose Oxidation by Pseudomonas fragi*", "The Journal of Biological Chemistry", Mar. 1961, pp. 629-634, vol. 236, No. 3.

Yim, H., et al., "Metabolic engineering of *Escherichia coli* for direct production of 1,4-butanediol", "Nature Chemical Biology", 2011, pp. 445-452, vol. 7, Publisher: npg, Nature America, Inc.

* cited by examiner

SEQUENCE LISTING

```
<160> NUMBER OF SEQ ID NOS: 56

<210> SEQ ID NO 1
<211> LENGTH: 559
<212> TYPE: PRT
<213> ORGANISM: Pseudomonas sp. 6-19

<400> SEQUENCE: 1

Met Ser Asn Lys Ser Asn Asp Glu Leu Lys Tyr Gln Ala Ser Glu Asn
1               5                   10                  15

Thr Leu Gly Leu Asn Pro Val Val Gly Leu Arg Gly Lys Asp Leu Leu
            20                  25                  30

Ala Ser Ala Arg Met Val Leu Arg Gln Ala Ile Lys Gln Pro Val His
        35                  40                  45

Ser Val Lys His Val Ala His Phe Gly Leu Glu Leu Lys Asn Val Leu
    50                  55                  60

Leu Gly Lys Ser Gly Leu Gln Pro Thr Ser Asp Asp Arg Arg Phe Ala
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Asp Glu Ser Asn
            100                 105                 110

Leu Ala Pro Lys Asp Val Ala Arg Gly His Phe Val Ile Asn Leu Met
```

```
            115                 120                 125
Thr Glu Ala Met Ala Pro Thr Asn Thr Ala Ala Asn Pro Ala Ala Val
    130                 135                 140
Lys Arg Phe Phe Glu Thr Gly Gly Lys Ser Leu Leu Asp Gly Leu Ser
145                 150                 155                 160
His Leu Ala Lys Asp Leu Val His Asn Gly Met Pro Ser Gln Val
                165                 170                 175
Asn Met Gly Ala Phe Glu Val Gly Lys Ser Leu Gly Val Thr Glu Gly
            180                 185                 190
Ala Val Val Phe Arg Asn Asp Val Leu Glu Leu Ile Gln Tyr Lys Pro
            195                 200                 205
Thr Thr Glu Gln Val Tyr Glu Arg Pro Leu Leu Val Val Pro Pro Gln
    210                 215                 220
Ile Asn Lys Phe Tyr Val Phe Asp Leu Ser Pro Asp Lys Ser Leu Ala
225                 230                 235                 240
Arg Phe Cys Leu Arg Asn Asn Val Gln Thr Phe Ile Val Ser Trp Arg
                245                 250                 255
Asn Pro Thr Lys Glu Gln Arg Glu Trp Gly Leu Ser Thr Tyr Ile Glu
            260                 265                 270
Ala Leu Lys Glu Ala Val Asp Val Val Thr Ala Ile Thr Gly Ser Lys
        275                 280                 285
Asp Val Asn Met Leu Gly Ala Cys Ser Gly Gly Ile Thr Cys Thr Ala
    290                 295                 300
Leu Leu Gly His Tyr Ala Ala Ile Gly Glu Asn Lys Val Asn Ala Leu
305                 310                 315                 320
Thr Leu Leu Val Ser Val Leu Asp Thr Thr Leu Asp Ser Asp Val Ala
                325                 330                 335
Leu Phe Val Asn Glu Gln Thr Leu Glu Ala Ala Lys Arg His Ser Tyr
            340                 345                 350
Gln Ala Gly Val Leu Glu Gly Arg Asp Met Ala Lys Val Phe Ala Trp
        355                 360                 365
Met Arg Pro Asn Asp Leu Ile Trp Asn Tyr Trp Val Asn Asn Tyr Leu
    370                 375                 380
Leu Gly Asn Glu Pro Pro Val Phe Asp Ile Leu Phe Trp Asn Asn Asp
385                 390                 395                 400
Thr Thr Arg Leu Pro Ala Ala Phe His Gly Asp Leu Ile Glu Leu Phe
                405                 410                 415
Lys Asn Asn Pro Leu Ile Arg Pro Asn Ala Leu Glu Val Cys Gly Thr
            420                 425                 430
Pro Ile Asp Leu Lys Gln Val Thr Ala Asp Ile Phe Ser Leu Ala Gly
        435                 440                 445
Thr Asn Asp His Ile Thr Pro Trp Lys Ser Cys Tyr Lys Ser Ala Gln
    450                 455                 460
Leu Phe Gly Gly Asn Val Glu Phe Val Leu Ser Ser Ser Gly His Ile
465                 470                 475                 480
Gln Ser Ile Leu Asn Pro Pro Gly Asn Pro Lys Ser Arg Tyr Met Thr
                485                 490                 495
Ser Thr Glu Val Ala Glu Asn Ala Asp Glu Trp Gln Ala Asn Ala Thr
            500                 505                 510
Lys His Thr Asp Ser Trp Trp Leu His Trp Gln Ala Trp Gln Ala Gln
        515                 520                 525
Arg Ser Gly Glu Leu Lys Lys Ser Pro Thr Lys Leu Gly Ser Lys Ala
    530                 535                 540
```

Tyr Pro Ala Gly Glu Ala Ala Pro Gly Thr Tyr Val His Glu Arg
545                 550                 555

<210> SEQ ID NO 2
<211> LENGTH: 524
<212> TYPE: PRT
<213> ORGANISM: Artificial Sequence
<220> FEATURE:
<223> OTHER INFORMATION: Pct540

<400> SEQUENCE: 2

Met Arg Lys Val Pro Ile Ile Thr Ala Asp Glu Ala Ala Lys Leu Ile
1               5                   10                  15

Lys Asp Gly Asp Thr Val Thr Thr Ser Gly Phe Val Gly Asn Ala Ile
                20                  25                  30

Pro Glu Ala Leu Asp Arg Ala Val Glu Lys Arg Phe Leu Glu Thr Gly
            35                  40                  45

Glu Pro Lys Asn Ile Thr Tyr Val Tyr Cys Gly Ser Gln Gly Asn Arg
    50                  55                  60

Asp Gly Arg Gly Ala Glu His Phe Ala His Glu Gly Leu Leu Lys Arg
65                  70                  75                  80

Tyr Ile Ala Gly His Trp Ala Thr Val Pro Ala Leu Gly Lys Met Ala
                85                  90                  95

Met Glu Asn Lys Met Glu Ala Tyr Asn Val Ser Gln Gly Ala Leu Cys
            100                 105                 110

His Leu Phe Arg Asp Ile Ala Ser His Lys Pro Gly Val Phe Thr Lys
        115                 120                 125

Val Gly Ile Gly Thr Phe Ile Asp Pro Arg Asn Gly Gly Gly Lys Val
130                 135                 140

Asn Asp Ile Thr Lys Glu Asp Ile Val Glu Leu Val Glu Ile Lys Gly
145                 150                 155                 160

Gln Glu Tyr Leu Phe Tyr Pro Ala Phe Pro Ile His Val Ala Leu Ile
                165                 170                 175

Arg Gly Thr Tyr Ala Asp Glu Ser Gly Asn Ile Thr Phe Glu Lys Glu
            180                 185                 190

Ala Ala Pro Leu Glu Gly Thr Ser Val Cys Gln Ala Val Lys Asn Ser
        195                 200                 205

Gly Gly Ile Val Val Gln Val Glu Arg Val Val Lys Ala Gly Thr
210                 215                 220

Leu Asp Pro Arg His Val Lys Val Pro Gly Ile Tyr Val Asp Tyr Val
225                 230                 235                 240

Val Val Ala Asp Pro Glu Asp His Gln Gln Ser Leu Asp Cys Glu Tyr
                245                 250                 255

Asp Pro Ala Leu Ser Gly Glu His Arg Arg Pro Glu Val Val Gly Glu
            260                 265                 270

Pro Leu Pro Leu Ser Ala Lys Lys Val Ile Gly Arg Arg Gly Ala Ile
        275                 280                 285

Glu Leu Glu Lys Asp Val Ala Val Asn Leu Gly Val Gly Ala Pro Glu
    290                 295                 300

Tyr Val Ala Ser Val Ala Asp Glu Glu Gly Ile Val Asp Phe Met Thr
305                 310                 315                 320

Leu Thr Ala Glu Ser Gly Ala Ile Gly Gly Val Pro Ala Gly Gly Val
                325                 330                 335

Arg Phe Gly Ala Ser Tyr Asn Ala Asp Ala Leu Ile Asp Gln Gly Tyr
            340                 345                 350

Gln Phe Asp Tyr Tyr Asp Gly Gly Leu Asp Leu Cys Tyr Leu Gly
    355                 360                 365

Leu Ala Glu Cys Asp Glu Lys Gly Asn Ile Asn Val Ser Arg Phe Gly
370                 375                 380

Pro Arg Ile Ala Gly Cys Gly Gly Phe Ile Asn Ile Thr Gln Asn Thr
385                 390                 395                 400

Pro Lys Val Phe Phe Cys Gly Thr Phe Thr Ala Gly Gly Leu Lys Val
                405                 410                 415

Lys Ile Glu Asp Gly Lys Val Ile Ile Val Gln Glu Gly Lys Gln Lys
                420                 425                 430

Lys Phe Leu Lys Ala Val Glu Gln Ile Thr Phe Asn Gly Asp Val Ala
            435                 440                 445

Leu Ala Asn Lys Gln Gln Val Thr Tyr Ile Thr Glu Arg Cys Val Phe
450                 455                 460

Leu Leu Lys Glu Asp Gly Leu His Leu Ser Glu Ile Ala Pro Gly Ile
465                 470                 475                 480

Asp Leu Gln Thr Gln Ile Leu Asp Val Met Asp Phe Ala Pro Ile Ile
                485                 490                 495

Asp Arg Asp Ala Asn Gly Gln Ile Lys Leu Met Asp Ala Ala Leu Phe
            500                 505                 510

Ala Glu Gly Leu Met Gly Leu Lys Glu Met Lys Ser
            515                 520

<210> SEQ ID NO 3
<211> LENGTH: 747
<212> TYPE: DNA
<213> ORGANISM: Caulobacter crescentus

<400> SEQUENCE: 3
atgtcctcag ccatctatcc cagcctgaag gcaagcgcg tcgtcatcac cggcggcggc      60
tcgggcatcg gggccggcct caccgccggc ttcgcccgtc agggcgcgga ggtgatcttc     120
ctcgacatcg ccgacgagga ctccagggct cttgaggccg agctggccgg ctcgccgatc     180
ccgccggtct acaagcgctg cgacctgatg aacctgagg cgatcaaggc ggtcttcgcc      240
gagatcggcg acgtcgacgt gctggtcaac aacgccggca tgacgaccg ccacaagctg      300 gccgacgtga ccgcgcccta tgggacgag cggatcaacg tcaacctgcg ccacatgctg      360
ttctgcaccc aggccgtcgc gccgggcatg aagaagcgtg gcggcggggc ggtgatcaac     420
ttcggttcga tcagctggca cctggggctt gaggacctcg tcctctacga aaccgccaag     480
gccggcatcg aaggcatgac ccgcgcgctg gcccgggagc tgggtcccga cgacatccgc     540
gtcacctgcg tggtgccggg caacgtcaag accaagcgcc aggagaagtg gtacacgccc     600
gaaggcgagg cccagatcgt ggcggcccaa tgcctgaagg ccgcatcgt cccggagaac      660 gtcgccgcgc tggtgctgtt cctggcctcg gatgacgcgt cgctctgcac cggccacgaa     720
tactggatcg acgccggctg gcgttga                                          747

<210> SEQ ID NO 4
<211> LENGTH: 870
<212> TYPE: DNA
<213> ORGANISM: Caulobacter crescentus

<400> SEQUENCE: 4
atgaccgctc aagtcacttg cgtatgggat ctgaaggcca cgttgggcga aggcccgatc      60
tggcatggcg acaccctgtg gttcgtcgac atcaagcagc gtaaaatcca caactaccac     120

```
cccgccaccg gcgagcgctt cagcttcgac gcgccggatc aggtgacctt cctcgcgccg    180
atcgtcggcg cgaccggctt tgtcgtcggt ctgaagaccg ggattcaccg cttccacccg    240
gccacgggct tcagcctgct gctcgaggtc gaggacgcgg cgctgaacaa ccgccccaac    300
gacgccacgg tcgacgcgca aggccgtctg tggttcggca ccatgcacga cggggaagag    360
aacaatagcg gctcgctcta tcggatggac ctcaccggcg tcgcccggat ggaccgcgac    420
atctgcatca ccaacggccc gtgcgtctcg cccgacggca agaccttcta ccacaccgac    480
accctggaaa agacgatcta cgccttcgac ctggccgagg acggcctgct gtcgaacaag    540
cgcgtcttcg tgcagttcgc cctgggcgac gatgtctatc cggacggttc ggtcgtcgat    600
tccgaaggct atctgtggac cgccctgtgg ggcggtttcg gcgcggtccg cttctcgccg    660
caaggcgacg ccgtgacgcg catcgaactg cccgccccca acgtcaccaa gccctgcttc    720
ggcgggcctg acctgaagac cctctatttc accaccgccc gcaagggcct gagcgacgag    780
accctggccc agtacccgct ggccggcggt gtgttcgccg ttccggtcga tgtggccggc    840
caaccccagc atgaggtccg ccttgtctaa                                     870

<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
agacaggaat tcatgtcctc agccatctat cccag                               35

<210> SEQ ID NO 6
<211> LENGTH: 33
<212> TYPE: DNA
<213> ORGANISM: Artificial Sequence
<220> FEATURE:
<223> OTHER INFORMATION: primer

<400> SEQUENCE: 6
agacagctgc agttagacaa ggcggacctc atg                                 33

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
atgactgacg ttgtcatcgt atcc                                           24

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
gatttgattg tctctctgcc gtc                                            23

<210> SEQ ID NO 9
<211> LENGTH: 29
<212> TYPE: DNA
```

<213> ORGANISM: Artificial Sequence
<220> FEATURE:
<223> OTHER INFORMATION: primer

<400> SEQUENCE: 9
agacaggcat gccgggcaag taccttgcc                               29

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
agacaggcat gctcagccca tatgcaggcc                              30

<210> SEQ ID NO 11
<211> LENGTH: 34
<212> TYPE: DNA
<213> ORGANISM: Artificial Sequence
<220> FEATURE:
<223> OTHER INFORMATION: primer

<400> SEQUENCE: 11
agacaggcat gcttgacaat taatcatccg gctc                         34

<210> SEQ ID NO 12
<211> LENGTH: 45
<212> TYPE: DNA
<213> ORGANISM: Artificial Sequence
<220> FEATURE:
<223> OTHER INFORMATION: primer

<400> SEQUENCE: 12
agacaggcat gcttaatata acttttata tgtgtttact atgtc              45

<210> SEQ ID NO 13
<211> LENGTH: 70
<212> TYPE: DNA
<213> ORGANISM: Artificial Sequence
<220> FEATURE:
<223> OTHER INFORMATION: primer

<400> SEQUENCE: 13
gcggaagcag ccaataagaa ggagaaggcg aatggctgag atgaaaaacc gacactatag    60
aacgcggccg                                                           70

<210> SEQ ID NO 14
<211> LENGTH: 70
<212> TYPE: DNA
<213> ORGANISM: Artificial Sequence
<220> FEATURE:
<223> OTHER INFORMATION: primer

<400> SEQUENCE: 14
gacgtgtttc gggcagactt cggagcagta gcccacgaaa gtacagctcc ccgcataggc    60
cactagtgga                                                           70

<210> SEQ ID NO 15
<211> LENGTH: 70
<212> TYPE: DNA
<213> ORGANISM: Artificial Sequence
<220> FEATURE:
<223> OTHER INFORMATION: primer

<400> SEQUENCE: 15
tgccgccagc taaacgcgtt tacggtggcg aagcggatgc agccgataag gcggaagcag    60
ccaataagaa                                                          70

<210> SEQ ID NO 16
<211> LENGTH: 70
<212> TYPE: DNA
<213> ORGANISM: Artificial Sequence
<220> FEATURE:
<223> OTHER INFORMATION: primer

<400> SEQUENCE: 16
aagtctttcg aactttctac tttgccctgc tgaatggccg cagccggatc gacgtgtttc    60
gggcagactt                                                          70

<210> SEQ ID NO 17
<211> LENGTH: 70
<212> TYPE: DNA
<213> ORGANISM: Artificial Sequence
<220> FEATURE:
<223> OTHER INFORMATION: primer

<400> SEQUENCE: 17
tttctctccc atcccttccc cctccgtcag atgaactaaa cttgttaccg gacactatag    60
aacgcggccg                                                          70

<210> SEQ ID NO 18
<211> LENGTH: 70
<212> TYPE: DNA
<213> ORGANISM: Artificial Sequence
<220> FEATURE:
<223> OTHER INFORMATION: primer

<400> SEQUENCE: 18
gcgcagcata tacaggctga aacctttggc ctgttcgagt ttgatctgcg ccgcataggc    60
cactagtgga                                                          70

<210> SEQ ID NO 19
<211> LENGTH: 70
<212> TYPE: DNA
<213> ORGANISM: Artificial Sequence
<220> FEATURE:
<223> OTHER INFORMATION: primer

<400> SEQUENCE: 19
tatgcccgat gatattcctt tcatcgggct atttaaccgt tagtgcctcc tttctctccc    60
atcccttccc                                                          70

<210> SEQ ID NO 20
<211> LENGTH: 70
<212> TYPE: DNA
<213> ORGANISM: Artificial Sequence
<220> FEATURE:
<223> OTHER INFORMATION: primer

<400> SEQUENCE: 20
tttgttttcg ccagttcgat cacttcatca ccgcgtccgc tgatgattgc gcgcagcata    60
tacaggctga                                                          70

<210> SEQ ID NO 21

```
<210> SEQ ID NO 21
<211> LENGTH: 70
<212> TYPE: DNA
<213> ORGANISM: Artificial Sequence
<220> FEATURE:
<223> OTHER INFORMATION: primer

<400> SEQUENCE: 21
tgaacttaac gcactcgtag agcgtgtaaa aaaagcccag cgtgaatatg gacactatag      60
aacgcggccg                                                            70

<210> SEQ ID NO 22
<211> LENGTH: 70
<212> TYPE: DNA
<213> ORGANISM: Artificial Sequence
<220> FEATURE:
<223> OTHER INFORMATION: primer

<400> SEQUENCE: 22
gcttttttct cagctttagc cggagcagct tctttcttcg ctgcagtttc ccgcataggc      60
cactagtgga                                                            70

<210> SEQ ID NO 23
<211> LENGTH: 72
<212> TYPE: DNA
<213> ORGANISM: Artificial Sequence
<220> FEATURE:
<223> OTHER INFORMATION: primer

<400> SEQUENCE: 23
aaaaaagttt aacattatca ggagagcatt atggctgtta ctaatgtcgc tgaacttaac      60
gcactcgtag ag                                                         72

<210> SEQ ID NO 24
<211> LENGTH: 72
<212> TYPE: DNA
<213> ORGANISM: Artificial Sequence
<220> FEATURE:
<223> OTHER INFORMATION: primer

<400> SEQUENCE: 24
aggggccgtt tatgttgcca gacagcgcta ctgattaagc ggattttttc gcttttttct      60
cagctttagc cg                                                         72

<210> SEQ ID NO 25
<211> LENGTH: 70
<212> TYPE: DNA
<213> ORGANISM: Artificial Sequence
<220> FEATURE:
<223> OTHER INFORMATION: primer

<400> SEQUENCE: 25
taccaaaggt gactggcaga atgaagtaaa cgtccgtgac ttcattcaga gacactatag      60
aacgcggccg                                                            70

<210> SEQ ID NO 26
<211> LENGTH: 70
<212> TYPE: DNA
<213> ORGANISM: Artificial Sequence
<220> FEATURE:
<223> OTHER INFORMATION: primer

<400> SEQUENCE: 26
gcgagttgaa acgtactgcg tagccagata cacggatggt cagctgcgga ccgcataggc      60
```

-continued

```
cactagtgga                                                            70

<210> SEQ ID NO 27
<211> LENGTH: 70
<212> TYPE: DNA
<213> ORGANISM: Artificial Sequence
<220> FEATURE:
<223> OTHER INFORMATION: primer

<400> SEQUENCE: 27
tgttacatgt ccgagcttaa tgaaaagtta gccacagcct gggaaggttt taccaaaggt    60
gactggcaga                                                            70

<210> SEQ ID NO 28
<211> LENGTH: 70
<212> TYPE: DNA
<213> ORGANISM: Artificial Sequence
<220> FEATURE:
<223> OTHER INFORMATION: primer

<400> SEQUENCE: 28
agattgagtg aaggtacgag taataacgtc ctgctgctgt tctttagtca gcgagttgaa    60
acgtactgcg                                                            70

<210> SEQ ID NO 29
<211> LENGTH: 70
<212> TYPE: DNA
<213> ORGANISM: Artificial Sequence
<220> FEATURE:
<223> OTHER INFORMATION: primer

<400> SEQUENCE: 29
ccttcgttca cagtggggaa gttttcggat ccatgacgag gagctgcacg gacactatag    60
aacgcggccg                                                            70

<210> SEQ ID NO 30
<211> LENGTH: 73
<212> TYPE: DNA
<213> ORGANISM: Artificial Sequence
<220> FEATURE:
<223> OTHER INFORMATION: primer

<400> SEQUENCE: 30
aatttgttgt gtacgggttt tcatgtgcag atgctccata gttatgtggt ggtccgcata    60
ggccactagt gga                                                        73

<210> SEQ ID NO 31
<211> LENGTH: 69
<212> TYPE: DNA
<213> ORGANISM: Artificial Sequence
<220> FEATURE:
<223> OTHER INFORMATION: primer

<400> SEQUENCE: 31
cattttaaat gagtagtctt agttgtgctg aacgaaaaga gcacaacgat ccttcgttca    60
cagtgggga                                                             69

<210> SEQ ID NO 32
<211> LENGTH: 70
<212> TYPE: DNA
<213> ORGANISM: Artificial Sequence
<220> FEATURE:
```

```
<223> OTHER INFORMATION: primer

<400> SEQUENCE: 32
aatgccttcc caacgcggtt gagtccactc tttctgtaat tcttcaattt gttgtgtacg    60
ggttttcatg                                                           70

<210> SEQ ID NO 33
<211> LENGTH: 70
<212> TYPE: DNA
<213> ORGANISM: Artificial Sequence
<220> FEATURE:
<223> OTHER INFORMATION: primer

<400> SEQUENCE: 33
cagcgcgcaa aaatcagctg ccacacaaca caacaaagcg aagcctactc gacactatag    60
aacgcggccg                                                           70

<210> SEQ ID NO 34
<211> LENGTH: 73
<212> TYPE: DNA
<213> ORGANISM: Artificial Sequence
<220> FEATURE:
<223> OTHER INFORMATION: primer

<400> SEQUENCE: 34
cagttactat catagccccg acaataaaac ttgccggggc ttttttgacg ctaccgcata    60
ggccactagt gga                                                       73

<210> SEQ ID NO 35
<211> LENGTH: 73
<212> TYPE: DNA
<213> ORGANISM: Artificial Sequence
<220> FEATURE:
<223> OTHER INFORMATION: primer

<400> SEQUENCE: 35
cagttactat catagccccg acaataaaac ttgccggggc ttttttgacg ctaccgcata    60
ggccactagt gga                                                       73

<210> SEQ ID NO 36
<211> LENGTH: 70
<212> TYPE: DNA
<213> ORGANISM: Artificial Sequence
<220> FEATURE:
<223> OTHER INFORMATION: primer

<400> SEQUENCE: 36
aaaccctgat aatcgctccg gttatttccg ggataaatgt actaccgcag ttactatcat    60
agccccgaca                                                           70

<210> SEQ ID NO 37
<211> LENGTH: 70
<212> TYPE: DNA
<213> ORGANISM: Artificial Sequence
<220> FEATURE:
<223> OTHER INFORMATION: primer

<400> SEQUENCE: 37
cctgtacacg gcgaggctct ccccccttgc cacgcgtgag aacgtaaaaa gacactatag    60
aacgcggccg                                                           70
```

```
<210> SEQ ID NO 38
<211> LENGTH: 70
<212> TYPE: DNA
<213> ORGANISM: Artificial Sequence
<220> FEATURE:
<223> OTHER INFORMATION: primer

<400> SEQUENCE: 38
gtaaaaaagg cagccatctg gctgccttag tctccccaac gtcttacgga ccgcataggc    60
cactagtgga                                                           70

<210> SEQ ID NO 39
<211> LENGTH: 70
<212> TYPE: DNA
<213> ORGANISM: Artificial Sequence
<220> FEATURE:
<223> OTHER INFORMATION: primer

<400> SEQUENCE: 39
tggcactgaa ttattttact ctgtgtaata aataaagggc gcttagatgc cctgtacacg    60
gcgaggctct                                                           70

<210> SEQ ID NO 40
<211> LENGTH: 71
<212> TYPE: DNA
<213> ORGANISM: Artificial Sequence
<220> FEATURE:
<223> OTHER INFORMATION: primer

<400> SEQUENCE: 40
caccgcgtaa tttcagcatt accggcacgt atcaattctg aataacacct gtaaaaaagg    60
cagccatctg g                                                         71

<210> SEQ ID NO 41
<211> LENGTH: 70
<212> TYPE: DNA
<213> ORGANISM: Artificial Sequence
<220> FEATURE:
<223> OTHER INFORMATION: primer

<400> SEQUENCE: 41
cggtgcgcga taaatcgaaa ctgggggggtt aataatggct gactcgcaac gacactatag    60
aacgcggccg                                                           70

<210> SEQ ID NO 42
<211> LENGTH: 70
<212> TYPE: DNA
<213> ORGANISM: Artificial Sequence
<220> FEATURE:
<223> OTHER INFORMATION: primer

<400> SEQUENCE: 42 gcattttcc ctaacccgcc aaaaagaacc tgaacgccgg gttattggtt ccgcataggc     60
cactagtgga                                                           70

<210> SEQ ID NO 43
<211> LENGTH: 70
<212> TYPE: DNA
<213> ORGANISM: Artificial Sequence
<220> FEATURE:
<223> OTHER INFORMATION: primer

<400> SEQUENCE: 43
```

```
ctttgccctg cgtgcttatg ccagcctggc aaccagcgcc gacaaaggcg cggtgcgcga    60
taaatcgaaa                                                          70
```

<210> SEQ ID NO 44
<211> LENGTH: 70
<212> TYPE: DNA
<213> ORGANISM: Artificial Sequence
<220> FEATURE:
<223> OTHER INFORMATION: primer

<400> SEQUENCE: 44

```
cacaaatgac gttgtcgcgc gggtaggcct gataagcgaa gcgctatcag gcattttttcc   60 ctaacccgcc                                                          70
```

<210> SEQ ID NO 45
<211> LENGTH: 70
<212> TYPE: DNA
<213> ORGANISM: Artificial Sequence
<220> FEATURE:
<223> OTHER INFORMATION: primer

<400> SEQUENCE: 45

```
gcgtatcttc ataccatgac tcataaagga gataccccga tgaccattac gacactatag   60
aacgcggccg                                                          70
```

<210> SEQ ID NO 46
<211> LENGTH: 70
<212> TYPE: DNA
<213> ORGANISM: Artificial Sequence
<220> FEATURE:
<223> OTHER INFORMATION: primer

<400> SEQUENCE: 46

```
accgcaggtc tgaaaagacc tgcgagtata tcagagctga atatgtcgcg ccgcataggc   60
cactagtgga                                                          70
```

<210> SEQ ID NO 47
<211> LENGTH: 73
<212> TYPE: DNA
<213> ORGANISM: Artificial Sequence
<220> FEATURE:
<223> OTHER INFORMATION: primer

<400> SEQUENCE: 47

```
ttcgtgaata agtggcttaa tattattcat tttaaagcaa gagtaaatct gcgtatcttc   60
ataccatgac tca                                                      73
```

<210> SEQ ID NO 48
<211> LENGTH: 70
<212> TYPE: DNA
<213> ORGANISM: Artificial Sequence
<220> FEATURE:
<223> OTHER INFORMATION: primer

<400> SEQUENCE: 48

```
tgttttctaa aattgcatta tccatggcga ctgccacttt ctactcctgg accgcaggtc   60
tgaaaagacc                                                          70
```

<210> SEQ ID NO 49
<211> LENGTH: 70
<212> TYPE: DNA
<213> ORGANISM: Artificial Sequence

```
<220> FEATURE:
<223> OTHER INFORMATION: primer

<400> SEQUENCE: 49
tgccttacac gccgcattta atcaataacc tttgaaaaca ggatgtagcg gacactatag     60
aacgcggccg                                                            70

<210> SEQ ID NO 50
<211> LENGTH: 70
<212> TYPE: DNA
<213> ORGANISM: Artificial Sequence
<220> FEATURE:
<223> OTHER INFORMATION: primer

<400> SEQUENCE: 50
gactgcggcg ctgcattaac tctttattgc tgttcattcg cattctccag ccgcataggc     60
cactagtgga                                                            70

<210> SEQ ID NO 51
<211> LENGTH: 70
<212> TYPE: DNA
<213> ORGANISM: Artificial Sequence
<220> FEATURE:
<223> OTHER INFORMATION: primer

<400> SEQUENCE: 51
gcaagccaga gtaaccccgg acgcacgctg cgagcggcac gtagtgtgga tgccttacac     60
gccgcattta                                                            70

<210> SEQ ID NO 52
<211> LENGTH: 70
<212> TYPE: DNA
<213> ORGANISM: Artificial Sequence
<220> FEATURE:
<223> OTHER INFORMATION: primer

<400> SEQUENCE: 52
gcgcggtcag cgaaaatcgg gtgaatttgc ccaacgccac ggggaatcgc ctgactgcgg     60
cgctgcatta                                                            70

<210> SEQ ID NO 53
<211> LENGTH: 70
<212> TYPE: DNA
<213> ORGANISM: Artificial Sequence
<220> FEATURE:
<223> OTHER INFORMATION: promoter

<400> SEQUENCE: 53
gcgcggtcag cgaaaatcgg gtgaatttgc ccaacgccac ggggaatcgc ctgactgcgg     60
cgctgcatta                                                            70

<210> SEQ ID NO 54
<211> LENGTH: 73
<212> TYPE: DNA
<213> ORGANISM: Artificial Sequence
<220> FEATURE:
<223> OTHER INFORMATION: promoter

<400> SEQUENCE: 54
ctgttgcagg tacttcttgt cgtactgttt tgtgctataa acggcgagtt tcatggtctg     60
tttcctgtgt gaa                                                        73
```

```
<210> SEQ ID NO 55
<211> LENGTH: 70
<212> TYPE: DNA
<213> ORGANISM: Artificial Sequence
<220> FEATURE:
<223> OTHER INFORMATION: promoter

<400> SEQUENCE: 55
cgtgggaacc cacagcccga gcgtcatcag cagcgtcaac ggcacaagaa taatcagtaa    60
taacagcgcg                                                            70

<210> SEQ ID NO 56
<211> LENGTH: 70
<212> TYPE: DNA
<213> ORGANISM: Artificial Sequence
<220> FEATURE:
<223> OTHER INFORMATION: promoter

<400> SEQUENCE: 56
cagcagaaag tcaaaaaatt ccagctcaaa gccaaaggac tcgttcacct gttgcaggta    60
cttcttgtcg                                                            70
```

RECOMBINANT MICROORGANISM HAVING ABILITY TO PRODUCE POLY(LACTATE-COGLYCOLATE) OR COPOLYMER THEREOF FROM XYLOSE AND METHOD FOR PREPARING POLY(LACTATE-COGLYCOLATE) OR COPOLYMER THEREOF BY USING SAME

CROSS-REFERENCE TO RELATED APPLICATIONS

This application is a U.S. national phase under the provisions of 35 U.S.C. § 371 of International Patent Application No. PCT/KR16/14574 filed Dec. 13, 2016, which in turn claims priority of Korean Patent Application No. 10-2016-0010549 filed Jan. 28, 2016. The disclosures of such International Patent Application No. PCT/KR16/14574 and Korean Patent Application No. 10-2016-0010549 are hereby incorporated herein by reference in their respective entireties, for all purposes.

TECHNICAL FIELD

The present invention relates to a recombinant microorganism having the ability to produce poly(lactate-co-glycolate) and its copolymers by using xylose as a single carbon source or using xylose and glucose simultaneously as carbon sources, and more particularly to a recombinant microorganism having the ability to produce poly(lactate-co-glycolate) copolymers without having to supply lactate and glycolate precursors from external sources, and a method of producing poly(lactate-co-glycolate) copolymers using the same.

BACKGROUND ART

Poly(lactate-co-glycolate) (PLGA), a random copolymer of lactate and glycolate, is a representative biodegradable polymer which is highly applicable as a general-purpose polymer or a medical polymer. Currently, PLGA can be produced by the direct polymerization reaction of lactate with glycolate, but this reaction mainly produces a PLGA having only a low molecular weight (1,000-5,000 Daltons). PLGA having a high molecular weight of 100,000 Daltons or more can be synthesized by the ring-opening polymerization of lactide with glycolide. Lactide and glycolide are cyclic diesters of lactate and glycolate, respectively, and are produced by thermal decomposition of a lactate oligomer and a glycolate oligomer, respectively. The ring-opening polymerization requires the use of a catalyst such as tin(II) 2-ethylhexanoate, tin(II) alkoxide, aluminum isopropoxide or the like. There is a method of producing a higher-molecular-weight polymer from a low-molecular-weight polymer, obtained by direct polymerization, by use of a chain-coupling agent. However, since the chain-coupling agent is used, the method of producing high-molecular weight PLGA has disadvantages in that the addition of an organic solvent or a chain coupling agent makes the process complex and in that this organic solvent or chain-coupling agent is not easily removed. Current commercial processes for producing high-molecular-weight PLGA use a method that comprises converting lactate and glycolate into lactide and glycolide, respectively, and then synthesizing PLGA by the ring-opening polymerization of lactide with glycolide.

Meanwhile, polyhydroxyalkanoate (PHA) is a polyester which is produced when microorganisms accumulate excess carbon sources as energy or carbon source-storing substances in the cells when subjected to an environment deficient in nutrients such as phosphorus, nitrogen, magnesium, oxygen and the like. Since PHA is completely biodegradable and may have physical properties similar to those of conventional synthetic polymers produced from petroleum, it is attracting attention as an environmentally friendly substitute for petroleum-based synthetic plastics.

It is known that PHA can be produced by a variety of organisms, including *Ralstonia eutropha*, *Pseudomonas*, *Bacillus*, recombinant *E. coli*, and the like, and may contain about 150 or more different monomers. Such PHA is roughly divided into SCL-PHA (short-chain-length PHA) having a short chain length monomer (3-5 carbon atoms) and MCL-PHA (medium-chain-length PHA) having a longer chain length monomer. PHA synthases, which are key enzymes that synthesize PHA, are roughly divided into four classes by the kind of monomer, which is used as a substrate, and the subunits of the enzyme (Qi et al., *FEMS Microbiol. Lett.*, 157:155, 1997; Qi et al., *FEMS Microbiol. Lett.*, 167:89, 1998; Langenbach et al., *FEMS Microbiol. Lett.*, 150:303, 1997; WO 01/55436; U.S. Pat. No. 6,143,952; WO 98/54329; WO 99/61624).

Glycolic acid is the simplest hydroxycarboxylic acid having two carbon atoms, and PHA that naturally contains glycolic acid has not been reported yet. However, glycolic acid together with polylactate is highly useful as a representative synthetic biopolymer, and thus various attempts have been made to insert it into a PHA monomer.

In a previous patent (U.S. Pat. No. 8,883,463 B2), the present inventors constructed an *E. coli* strain, which produces glycolate by using glucose as a carbon source without having to add an external precursor, by engineering the glyoxylate shunt pathway, and found that PLGA was produced from glucose by culturing the *E. coli* strain transformed with a gene encoding *Clostridium propionicum*-derived propionyl-CoA transferase (Pct), which is an enzyme that converts lactate and glycolate into lactyl-CoA and glycolyl-CoA, respectively, and a gene encoding polyhydroxyalkanoate (PHA) synthase (PhaC1) which can use lactyl-CoA and glycolyl-CoA as substrates.

Accordingly, the present inventors have made extensive efforts to develop a recombinant *E. coli* strain capable of producing a PLGA having a high content of a glycolate fraction with higher efficiency by using xylose as a main carbon source without having to add glycolate from an external source. As a result, the present inventors have constructed a recombinant microorganism expressing *Clostridium propionicum*-derived propionyl-CoA transferase, *Pseudomonas* sp. 6-19-derived PHA synthase, xylose dehydrogenase and xylonolactonase, and have found that the recombinant microorganism produces poly(lactate-co-glycolate) and its copolymers by using xylose as a single carbon source or using xylose and glucose simultaneously as carbon sources, thereby completing the present invention.

DISCLOSURE OF INVENTION

Technical Problem

It is an object of the present invention to provide a recombinant microorganism which can produce a high concentration of poly(lactate-co-glycolate) and various poly(lactate-co-glycolate) copolymers without external addition of glycolate.

Another object of the present invention is to provide a method of producing poly(lactate-co-glycolate) using a recombinant microorganism which can produce a high concentration of poly(lactate-co-glycolate) and various poly (lactate-co-glycolate) copolymers without external addition of glycolate.

Technical Solution

To achieve the above object, the present invention provides a recombinant microorganism having the ability to produce poly(lactate-co-glycolate), wherein a polyhydroxyalkanoate synthase-encoding gene, a propionyl-CoA transferase-encoding gene, a xylose dehydrogenase-encoding gene, and a xylonolactonase-encoding gene are introduced in a microorganism having the ability to produce lactate from pyruvic acid, and to a method of producing poly(lactate-co-glycolate) using the same.

The present invention also provides a recombinant microorganism having the ability to produce poly(lactate-co-glycolate-co-3-hydroxybutyrate), wherein a polyhydroxyalkanoate synthase-encoding gene, a propionyl-CoA transferase-encoding gene, a xylose dehydrogenase-encoding gene, a xylonolactonase-encoding gene, a beta-ketothiolase-encoding gene, and an acetoacetyl-CoA reductase-encoding gene are introduced in a microorganism, and to a method of producing poly(lactate-co-glycolate-co-3-hydroxybutyrate) using the same.

The present invention also provides a recombinant microorganism having the ability to produce poly(lactate-co-glycolate-co-4-hydroxybutyrate), wherein a polyhydroxyalkanoate synthase-encoding gene, a propionyl-CoA transferase-encoding gene, a xylose dehydrogenase-encoding gene, and a xylonolactonase-encoding gene, a CoA-dependent succinate semialdehyde dehydrogenase-encoding gene, and a 4-hydroxybutyrate dehydrogenase-encoding gene are introduced in a microorganism, and to a method of producing poly(lactate-co-glycolate-co-4-hydroxybutyrate) using the same.

BEST MODE FOR CARRYING OUT THE INVENTION

Figure 1:
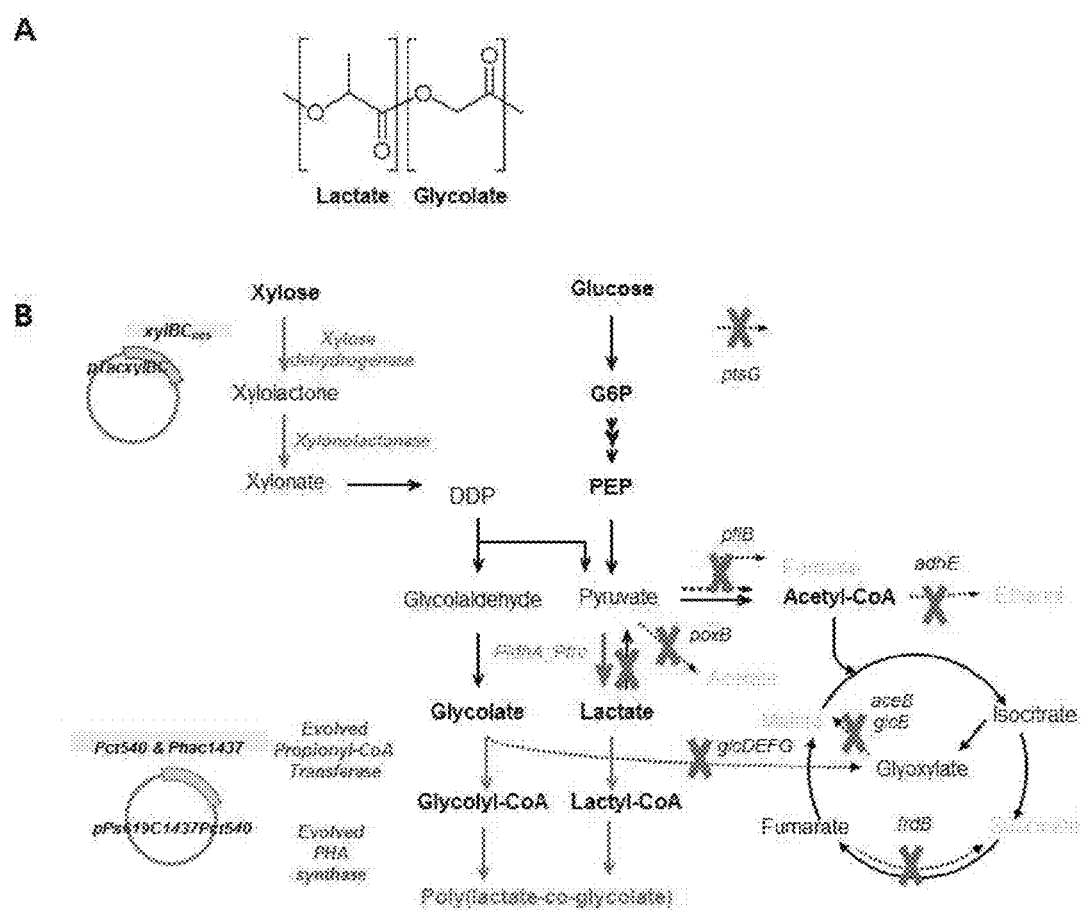
FIG. 1A shows the chemical formula of a PLGA produced in the present invention.
FIG. 1B shows a PLGA production pathway provided by metabolic engineering performed in the present invention.
Figure 2:
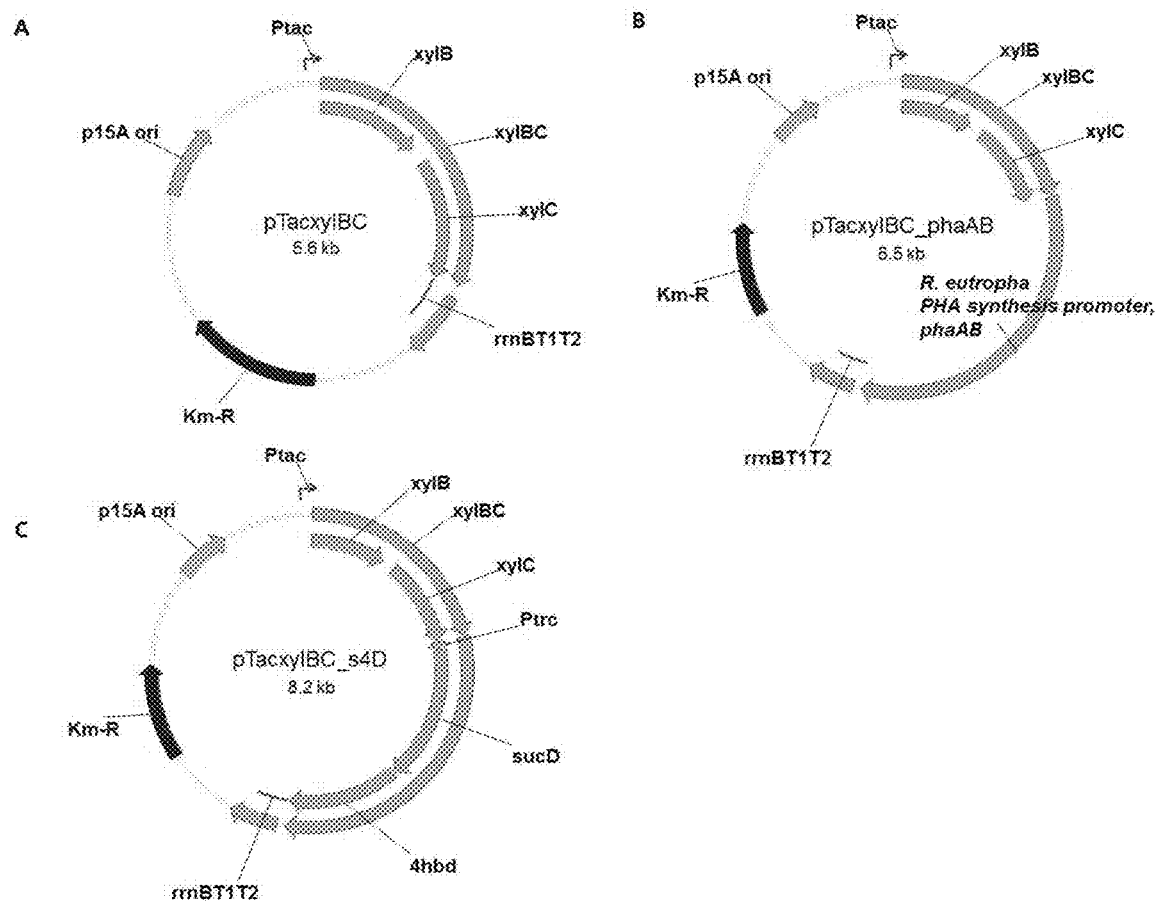
FIG. 2A shows a pTacxylBC plasmid.
FIG. 2B shows a pTacxylBC_phaAB plasmid.
FIG. 2C shows a pTacxylBC_s4D plasmid.

The patent or application file contains at least one drawing executed in color. Copies of this patent or patent application publication with color drawing(s) will be provided by the Office upon request and payment of the necessary fee.

The present inventors have attempted to develop a recombinant E. coli strain capable of producing a PLGA having a high content of a glycolate fraction with higher efficiency by using xylose rather than glucose as a main carbon source without having to add glycolate from an external source, as well as E. coli strains capable of producing various polymers comprising lactate and glycolate, and have found that a PLGA, which has a high content of a glycolate fraction, and poly(lactate-co-glycolate-co-2-hydroxybutyrate) can be produced at high concentrations, when Clostridium propionicum-derived propionyl-CoA transferase, Pseudomonas sp. 6-19-derived PHA synthase, xylose dehydrogenase and xylonolactonase are introduced, when a glucose PTS enzyme IIBC component-encoding gene (ptsG), an aldehyde-alcohol dehydrogenase-encoding gene (adhE), a pyruvate-formate lyase-encoding gene (pflB), a fumarate reductase-encoding gene (frdB), a pyruvate oxidase-encoding gene (poxB), a lactate dehydrogenase-encoding gene (dld), a malate synthase-encoding gene (aceB), a glycolate oxidase-encoding gene (glcDEFG), and another malate synthase-encoding gene (glcB) are deleted, and when the chromosomal promoter of a lactate dehydrogenase-encoding gene (ldhA) is replaced with a trc promoter.

Furthermore, it has been found that when a beta-ketothiolase-encoding gene (phaA) and an acetoacetyl-CoA reductase-encoding gene (phaB) are additionally introduced into the developed recombinant E. coli strain without supplying external precursors, the recombinant strain produces poly(lactate-co-glycolate-co-3-hydroxybutyrate), and when a CoA-dependent succinate semialdehyde dehydrogenase-encoding gene (sucD) and a 4-hydroxybutyrate dehydrogenase-encoding gene (4hbD) are additionally introduced, the recombinant strain produces poly(lactate-co-glycolate-co-4-hydroxybutyrate). Besides, it has been found that poly(lactate-co-glycolate-co-2-hydroxyisovalerate), poly(lactate-co-glycolate-co-5-hydroxyvalerate), and poly(lactate-co-glycolate-co-6-hydroxyhexanoate) can be produced by a method that supplies external precursors.

Therefore, in one aspect, the present invention is directed to a recombinant microorganism having the ability to produce poly(lactate-co-glycolate), wherein a polyhydroxyalkanoate synthase-encoding gene, a propionyl-CoA transferase-encoding gene and xylose dehydrogenase- and xylonolactonase-encoding genes are introduced in a microorganism having the ability to producing lactyl-CoA from pyruvic acid, and to a method of producing poly(lactate-co-glycolate) using the same.

In the present invention, the polyhydroxyalkanoate synthase may be Pseudomonas sp. 6-19-derived PHA synthase or a mutant enzyme of PHA synthase, which has an amino acid sequence selected from the following amino acid sequences:

an amino acid sequence comprising at least one mutation selected from the group consisting of E130D, S325T, S477G, S477F, S477Y, S477G and Q481K in the amino acid sequence of SEQ ID NO: 1; an amino acid sequence (PhaC1202) comprising mutations of E130D and Q481K in the amino acid sequence of SEQ ID NO: 1; an amino acid sequence (PhaC1301) comprising mutations of E130D, S325T and Q481K in the amino acid sequence of SEQ ID NO: 1; an amino acid sequence (PhaC1310) comprising mutations of E130D, S477F and Q481K in the amino acid sequence of SEQ ID NO: 1; an amino acid sequence (PhaC1437) comprising mutations of E130D, S325T, S477G and Q481K in the amino acid sequence of SEQ ID NO: 1; and an amino acid sequence (PhaC1439) comprising mutations of E130D, S325T, S477F and Q481K in the amino acid sequence of SEQ ID NO: 1.

In the present invention, the xylose dehydrogenase- and xylonolactonase-encoding genes may be derived from *Caulobacter crescentus*, and recombinant microorganisms may use the Dahms pathway by introducing the genes.

In the present invention, the xylose dehydrogenase- and xylonolactonase-encoding genes may have the nucleotide sequences of SEQ ID NOS: 3 and 4, respectively.

A method for producing poly(lactate-co-glycolate) according to the present invention comprises the steps of: (a) producing poly(lactate-co-glycolate) by culturing the above-described recombinant microorganism having the ability to produce poly(lactate-co-glycolate); and (b) recovering the produced poly(lactate-co-glycolate), wherein a carbon source which is used in the culturing may be either xylose which is supplied alone or xylose and glucose which are supplied simultaneously.

The present inventors performed metabolic engineering of an *E. coli* strain in order to construct an *E. coli* mutant capable of producing PLGA directly from a biomass-derived carbon source such as xylose without external addition of glycolate. In addition, the present inventors confirmed that the *E. coli* XL1-Blue strain had the genes involved in the metabolic pathway that produces glycolate via glyoxylate, but it did not naturally produce glycolate during culture. Thus, enhancement of the glycolate metabolic pathway and optimization of metabolic flux to glycolate were performed.

Regarding a metabolic pathway capable of producing glycolate in *E. coli*, isocitrate which is a metabolite forming the TCA cycle is converted to glyoxylate (glyoxylate shunt), and then the glyoxylate is converted to glycolate by glyoxylate enzyme. In other words, isocitrate is converted to glyoxylate by isocitrate lyase in the isocitrate node or converted to 2-ketoglutarate by isocitrate dehydrogenase and fluxes to the TCA cycle. This metabolic flux mechanism is regulated by phosphorylation/dephosphorylation of isocitrate dehydrogenase and regulated by various regulators. Previously, an attempt was made to produce PLGA from glucose by use of this metabolic pathway (U.S. Pat. No. 8,883,463 B2).

In the present invention, an attempt was made to construct an *E. coli* strain that produces a high concentration of PLGA by using xylose as a main carbon source, in view of the fact that glycolate can be produced from a xylose utilization pathway called the Dahms pathway.

Regarding the Dahms pathway, when a strain such as *Caulobacter* uses xylose as a carbon source, xylose is converted sequentially into xylonolactone, xylonate, and 2-dehydro-3-deoxy-pentonate which is then separated into glycolaldehyde and pyruvate by aldolase, and the glycolaldehyde is converted into glycolate by aldehyde dehydrogenase (see FIG. 1B). When an *E. coli* strain uses xylose as a carbon source, xylose enters the cells by a transporter, and then is converted by xylose isomerase and xylulose and metabolized via a pentose phosphate pathway, not the Dahms pathway. Thus, an attempt was made to construct the Dahms pathway in *E. coli* by introducing external genes into a microorganism that uses the Dahms pathway. Since it is known that enzymes downstream of the Dahms pathway are present in *E. coli*, xylose dehydrogenase and xylonolactonase upstream of the Dahms pathway were amplified from the chromosome of *Caulobacter crescentus*, thereby constructing a pTacxylBC plasmid. The pTacxylBC vector was transformed into the *E. coli* XL1-Blue strain which was then cultured in MR medium containing 20 g/l of xylose as a single carbon source, and as a result, 0.89 g/L of glycolate was produced.

In the present invention, the chromosomal promoter of a lactate dehydrogenase-encoding gene (ldhA) of the recombinant microorganism may be replaced with a strong promoter selected from the group consisting of trc, tac, pBAD, trp, lacUV5, and T7.

In addition to having an increased ability to produce PLGA, the strain constructed in the present invention may use glucose and xylose simultaneously, and thus can produce a PLGA polymer directly from a biomass hydrolysate by using, as a carbon source, lignocellulosic biomass such as waste wood, rice straw or the like, which is a non-refined carbon source, is not used for food, and is most abundant on the Earth, indicating that the price of the substrate can be greatly reduced.

In the present invention, a glucose PTS enzyme IIBC component-encoding gene may be deleted from the recombinant microorganism.

In the present invention, an aldehyde-alcohol dehydrogenase-encoding gene (adhE), a pyruvate-formate lyase-encoding gene (pflB), a fumarate reductase-encoding gene, and a pyruvate oxidase-encoding gene may further be deleted from the recombinant microorganism.

In the present invention, a dld gene that is another lactate dehydrogenase-encoding gene may further be deleted from the recombinant microorganism.

In the present invention, a malate synthase-encoding gene and a glycolate oxidase-encoding gene may further be deleted from the recombinant microorganism.

Figure 3:
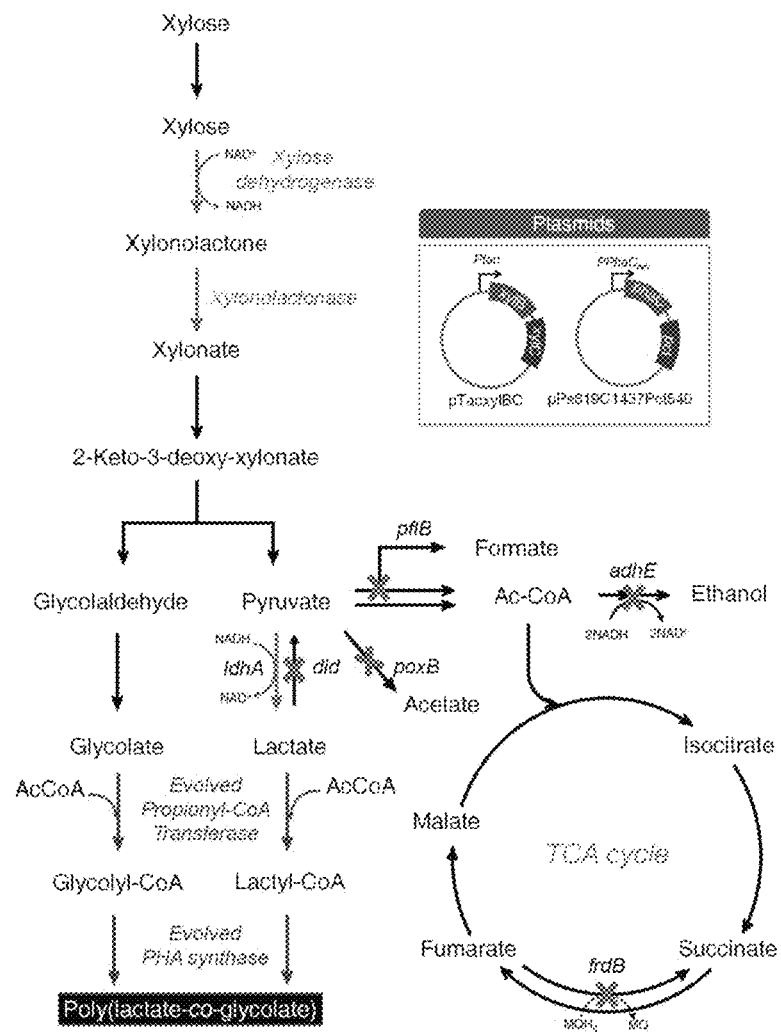
FIG. 3 shows a poly(lactate-co-glycolate) production pathway which uses xylose as a single carbon source by metabolic engineering performed in the present invention.

In an example of the present invention, since lactate which is another monomer of PLGA is produced using pyruvate as a precursor, it is important not to reduce to flux to lactate by the conversion of pyruvate to each of acetate and formate. Thus, in one example of the present invention, poxB (pyruvate oxidase) and pflB (pyruvate-formate lyase), which are genes involved in pyruvate conversion, were deleted, and the frdB (fumarate reductase) gene, known to prevent the production of the potential by-product succinate and have the effect of increasing lactate production, was also deleted. In addition, in order to increase a pool of acetyl-CoA functioning to provide Coenzyme A during the conversion of lactate and glycolate into lactyl-CoA and glycol-CoA by Pct540 and in order to prevent the production of ethanol which is a by-product in *E. coli* fermentation, the adhE gene was also deleted, thereby constructing an X15 strain. The X15 strain constructed as described above produced 1.06 g/L of glycolate (FIG. 3).

In this case, however, lactate was not produced. For this reason, in order to increase lactate production, the existing promoter of the ldhA gene corresponding to lactate dehydrogenase, which is an enzyme that converts pyruvate to lactate, was replaced with a stronger trc promoter, thereby constructing an X15-p strain. As a result, it was confirmed that the amount of lactate produced increased by a very small amount, and up to 0.07 g/l of lactate was produced (FIG. 3). It is believed that maintenance of a stronger lactate flux is important for PLGA production, and an effort was made to prevent the reduction of lactate with time. *E. coli* has another lactate dehydrogenase-encoding gene (dld) in addition to ldhA. Assuming that the dld gene would convert lactate again to pyruvate, the dld gene was deleted, thereby constructing an X15ld strain. In the case of the X15ld strain, the amount of lactate produced greatly increased to 0.67 g/L and also showed no tendency to decrease with culture time, and at the same time, 0.95 g/L of glycolate was also produced (FIG. 3).

Thus, in an example of the present invention, a recombinant microorganism having the ability to produce poly(lactate-co-glycolate) copolymers was produced wherein a polyhydroxyalkanoate synthase-encoding gene, a propionyl-CoA transferase-encoding gene, and xylose dehydrogenase and xylonolactonase-encoding genes are introduced, wherein a glucose PTS enzyme IIBC component-encoding gene (ptsG), an aldehyde-alcohol dehydrogenase-encoding gene (adhE), a pyruvate-formate lyase-encoding gene (pflB), a fumarate reductase-encoding gene (frdB), a pyruvate oxidase-encoding gene (poxB), a lactate dehydrogenase-encoding gene (dld), a malate synthase-encoding gene (aceB), a glycolate oxidase-encoding gene (glcDEFG), and another malate synthase-encoding gene (glcB) are deleted, and wherein the chromosomal promoter of a lactate dehydrogenase-encoding gene (ldhA) is replaced with a trc promoter.

In another aspect, the present invention is directed to a recombinant microorganism having the ability to produce poly(lactate-co-glycolate-co-3-hydroxybutyrate), wherein a polyhydroxyalkanoate synthase-encoding gene, a propionyl-CoA transferase-encoding gene, a xylose dehydrogenase-encoding gene, and a xylonolactonase-encoding gene, a beta-ketothiolase-encoding gene, and an acetoacetyl-CoA reductase-encoding gene are introduced in a microorganism having the ability to produce lactyl-CoA from pyruvic acid, and to a method of producing poly(lactate-co-glycolate-co-3-hydroxybutyrate) using the same.

A method for producing poly(lactate-co-glycolate-co-3-hydroxybutyrate) according to the present invention comprises the steps of: (a) producing poly(lactate-co-glycolate-co-3-hydroxybutyrate) by culturing the above-described recombinant microorganism having the ability to produce poly(lactate-co-glycolate-co-3-hydroxybutyrate); and (b) recovering the produced poly(lactate-co-glycolate-co-3-hydroxybutyrate), wherein a carbon source which is used in the culturing may be either xylose which is supplied alone or xylose and glucose which are supplied simultaneously.

In the present invention, the polyhydroxyalkanoate synthase may be *Pseudomonas* sp. 6-19-derived PHA synthase or a mutant enzyme of PHA synthase, which has an amino acid sequence selected from the following amino acid sequences:

an amino acid sequence comprising at least one mutation selected from the group consisting of E130D, S325T, S477G, S477F, S477Y, S477G and Q481K in the amino acid sequence of SEQ ID NO: 1; an amino acid sequence (PhaC1202) comprising mutations of E130D and Q481K in the amino acid sequence of SEQ ID NO: 1; an amino acid sequence (PhaC1301) comprising mutations of E130D, S325T and Q481K in the amino acid sequence of SEQ ID NO: 1; an amino acid sequence (PhaC1310) comprising mutations of E130D, S477F and Q481K in the amino acid sequence of SEQ ID NO: 1; an amino acid sequence (PhaC1437) comprising mutations of E130D, S325T, S477G and Q481K in the amino acid sequence of SEQ ID NO: 1; and an amino acid sequence (PhaC1439) comprising mutations of E130D, S325T, S477F and Q481K in the amino acid sequence of SEQ ID NO: 1.

In the present invention, the propionyl-CoA transferase may be a Pct540 enzyme represented by an amino acid sequence of SEQ ID NO: 2.

In the present invention, a gene selected from the group consisting of a glucose PTS enzyme IIBC component-encoding gene, an aldehyde-alcohol dehydrogenase-encoding gene, a pyruvate-formate lyase-encoding gene, a fumarate reductase-encoding gene, a pyruvate oxidase-encoding gene, a dld gene that is a lactate dehydrogenase-encoding gene, a malate synthase-encoding gene, and a glycolate oxidase-encoding gene may further be deleted from the recombinant microorganism.

In still another aspect, the present invention is directed to a recombinant microorganism having the ability to produce poly(lactate-co-glycolate-co-4-hydroxybutyrate), wherein a polyhydroxyalkanoate synthase-encoding gene, a propionyl-CoA transferase-encoding gene, a xylose dehydrogenase-encoding gene, and a xylonolactonase-encoding gene, a CoA-dependent succinate semialdehyde dehydrogenase-encoding gene, and a 4-hydroxybutyrate dehydrogenase-encoding gene are introduced in a microorganism having the ability to produce lactyl-CoA from pyruvic acid, and to a method of producing poly(lactate-co-glycolate-co-4-hydroxybutyrate) using the same.

A method for producing poly(lactate-co-glycolate-co-4-hydroxybutyrate) according to the present invention comprises the steps of: (a) producing poly(lactate-co-glycolate-co-4-hydroxybutyrate) by culturing the above-described recombinant microorganism having the ability to produce poly(lactate-co-glycolate-co-4-hydroxybutyrate); and (b) recovering the produced poly(lactate-co-glycolate-co-4-hydroxybutyrate), wherein a carbon source which is used in the culturing may be either xylose which is supplied alone or xylose and glucose which are supplied simultaneously. Furthermore, isoleucine and/or 2-hydroxyisovalerate as a precursor may be added during the culturing.

In the present invention, the polyhydroxyalkanoate synthase may be *Pseudomonas* sp. 6-19-derived PHA synthase or a mutant enzyme of PHA synthase, which has an amino acid sequence selected from the following amino acid sequences:

an amino acid sequence comprising at least one mutation selected from the group consisting of E130D, S325T, S477G, S477F, S477Y, S477G and Q481K in the amino acid sequence of SEQ ID NO: 1; an amino acid sequence (PhaC1202) comprising mutations of E130D and Q481K in the amino acid sequence of SEQ ID NO: 1; an amino acid sequence (PhaC1301) comprising mutations of E130D, S325T and Q481K in the amino acid sequence of SEQ ID NO: 1; an amino acid sequence (PhaC1310) comprising mutations of E130D, S477F and Q481K in the amino acid sequence of SEQ ID NO: 1; an amino acid sequence (PhaC1437) comprising mutations of E130D, S325T, S477G and Q481K in the amino acid sequence of SEQ ID NO: 1; and an amino acid sequence (PhaC1439) comprising mutations of E130D, S325T, S477F and Q481K in the amino acid sequence of SEQ ID NO: 1.

In the present invention, the propionyl-CoA transferase may be a Pct540 enzyme represented by an amino acid sequence of SEQ ID NO: 2.

In the present invention, a gene selected from the group consisting of a glucose PTS enzyme IIBC component-encoding gene, an aldehyde-alcohol dehydrogenase-encoding gene, a pyruvate-formate lyase-encoding gene, a fumarate reductase-encoding gene, a pyruvate oxidase-encoding gene, a dld gene that is a lactate dehydrogenase-encoding gene, a malate synthase-encoding gene, and a glycolate oxidase-encoding gene may further be deleted from the recombinant microorganism.

As used herein, "deletion" means that a gene is modified by substitution, deletion or mutation of the gene so that the protein encoded by the gene cannot exhibit its original function.

In the present invention, xylose and glucose may be used simultaneously as carbon sources through the deletion of a glucose PTS enzyme IIBC component-encoding gene (ptsG).

In the present invention, the chromosomal promoter of a lactate dehydrogenase-encoding gene (ldhA) may be replaced with a trc promoter, and a lactate dehydrogenase-encoding gene (dld) may be deleted from the recombinant microorganism.

In the present invention, a malate synthase-encoding gene (aceB), a glycolate oxidase-encoding gene (glcDEFG), and another malate synthase-encoding gene (glcB) may be deleted from the recombinant microorganism.

In the present invention, an E. coli strain that produces PLGA, a non-naturally-occurring polymer, was developed, and the metabolic pathway of E. coli was engineered so that a PLGA having various monomer fractions could be produced at high concentration. In addition, the present invention is directed to a method for producing copolymers, comprising the steps of: producing poly(lactate-co-glycolate-co-3-hydroxybutyrate), poly(lactate-co-glycolate-co-4-hydroxybutyrate), or poly(lactate-co-glycolate-co-2-hydroxybutyrate) without supplying external precursors, and recovering the produced poly(lactate-co-glycolate) copolymer.

In yet another aspect, the present invention is directed to a method for producing poly(lactate-co-glycolate-co-hydroxycarboxylic acid) comprising the steps of: (a) producing poly(lactate-co-glycolate-co-hydroxycarboxylic acid) by culturing the above-described recombinant microorganism in the presence of hydroxycarboxylic acid; and (b) recovering the produced poly(lactate-co-glycolate-co-hydroxycarboxylic acid).

In the present invention, the hydroxycarboxylic acid may be selected from the group consisting of 2-hydroxyisovalerate, 5-hydroxyvalerate, and 6-hydroxyhexanoate.

The present invention provides a method for producing poly(lactate-co-glycolate), comprising a step of producing and recovering poly(lactate-co-glycolate-co-2-hydroxyisovalerate), poly(lactate-co-glycolate-co-5-hydroxyvalerate), or poly(lactate-co-glycolate-co-6-hydroxyhexanoate) by supplying various precursors from the recombinant microorganism having the ability to produce poly(lactate-co-glycolate).

In one example of the present invention, the recombinant E. coli X17ld-p strain that expresses $Pct540_{Cp}$, $PhaC1437_{Ps6-19}$, xylose dehydrogenase and xylonolactonase derived from C. crescentus, produced poly(68.4 mol % lactate-co-31.6 mol % glycolate) at a concentration of 4.5 wt %. This is the first result demonstrating that poly (lactate-co-glycolate) was produced in the metabolically engineered E. coli strain using xylose as a main carbon source.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Construction of Plasmids for Genes Involved in PLGA Production, Strains, and Culture Method The strains, plasmids and primers used in the following Examples are shown in Tables 1 and 2 below.

1-1: Construction of Plasmid pTacxylBC

Since the xylose dehydrogenase-encoding gene xylB and xylonolactonase-encoding gene xylC are present as an operon on the chromosome of a Caulobacter crescentus strain obtained from the KCTC, the xylB and xylC genes were amplified simultaneously by PCR using the xylBC_F and xylBC_R primers shown in Table 2 below, and were then cloned into a pTac15k vector (Table 1) through EcoRI and PstI restriction enzyme sites so that they could be expressed under the control of a trc promoter.

1-2: Construction of Plasmid pTacxylBC_phaAB

Using a pCnCAB vector, obtained by cloning a phaCAB operon and its promoter from Ralstonia eutropha (KCTC No. 22469), as a template, inverse PCR was performed using two primers (Pcncab_invF, and Pcncab_invR), thereby constructing a pCnAB from which phaC was deleted. The R. eutropha PHA biosynthesis promoter and phaAB gene from the pCnAB plasmid were amplified by PCR using two primers (phaAB_F, and phaAB_R), and then cloned into a pTacxylBC vector through a SphI restriction enzyme site, thereby constructing a pTacxylBC_phaAB vector.

1-3: Construction of Plasmid pTacxylBC_s4D

A DNA corresponding to trc promoter-sucD-4hbD from a pTrc99s4 plasmid was amplified by PCR using two primers (s4D_F and s4D_R), and then cloned into a pTacxylBC plasmid via a SphI restriction enzyme site.

1-4: Culture Conditions and Analysis Method 100 mM MOPS-containing MR medium used to produce a PLGA copolymer in each recombinant E. coli strain in the Examples of the present invention contained, per liter, 6.67 g $KH_2PO_4$, 4 g $(NH_4)_2HPO_4$, 0.8 g $MgSO_4.H_2O$, 0.8 g citric acid, 0.8 g/l of $MgSO_4.H_2O$, 100 mM (3-morpholinopropane-1-sulfonic acid) MOPS and 5 ml of a trace metal solution. The trace metal solution contains, per liter, 0.5 M HCl, 10 g $FeSO_4.H_2O$, 2 g $CaCl_2$), 2.2 g $ZnSO_4.H_2O$, 0.5 g $MnSO_4.H_2O$, 1 g $CuSO_4.H_2O$, 0.1 g $(NH_4)_6Mo_7O_{24}.H_2O$, and 0.02 g $Na_2B_4O_7.10H_2O$.

In culture of each strain, seed culture was performed by shake culture in a 25 mL tube containing 5 mL of LB medium at 30° C. overnight, and 1 mL of the culture was inoculated into a 250 mL flask containing 100 mL of 100 mM MOPS-containing MR medium supplemented with 10 g/L of xylose and 10 g/L of glucose and was shake-cultured at 30° C. for 96 hours.

For expression of the ldhA gene under the control of the trc promoter, 1 mM IPTG was added when the $OD_{600}$ value reached 0.4-0.6. If necessary, 50 μg/mL of ampicillin, 30 μg/mL of kanamycin and 10 μg/mL of thiamine were added to the medium.

The genetic characteristics of the recombinant strains and plasmids used in the present invention are shown in Table below, and primers used to construct the recombinant strains and the plasmids in the present invention are shown in Table 2 below.

TABLE 1

Strains and plasmids used

| Strains or plasmids | Features[a] | Cited references/sources |
|---|---|---|
| Strains | | |
| XL1-Blue | recA1 endA1 gyrA96 thi-1 hsdR17 supE44 relA1 lac [F' proAB lacI$^q$ZΔM15 Tn10 (Tet$^R$)] | Stratagene[b] |
| X15 | XL1-Blue ΔadhE ΔpflB ΔfrdB ΔpoxB | the present invention |
| X15l | XL1-Blue ΔadhE ΔpflB ΔfrdB ΔpoxB PldhA::Ptrc | the present invention |
| X15ld | XL1-Blue ΔadhE ΔpflB ΔfrdB ΔpoxB PldhA::Ptrc Δdld | the present invention |
| XB-p | XL1-Blue ΔptsG | the present invention |
| X15-p | XL1-Blue ΔadhE ΔpflB ΔfrdB ΔpoxB ΔptsG | the present invention |
| X15l-p | XL1-Blue ΔadhE ΔpflB ΔfrdB ΔpoxB ΔptsG PldhA::Ptrc | the present invention |
| X15ld-p | XL1-Blue ΔadhE ΔpflB ΔfrdB ΔpoxB ΔptsG PldhA::Ptrc Δdld | the present invention |
| X17ld-p | XL1-Blue ΔadhE ΔpflB ΔfrdB ΔpoxB ΔptsG PldhA::Ptrc Δdld ΔaceB ΔglcDEFGB | the present invention |
| X15ld-pi | XL1-Blue ΔadhE ΔpflB ΔfrdB ΔpoxB ΔptsG PldhA::Ptrc Δdld ΔilvA | the present invention |
| X17ld-pyg | XL1-Blue ΔadhE ΔpflB ΔfrdB ΔpoxB ΔptsG PldhA::Ptrc Δdld ΔaceB ΔglcDEFGB ΔyneI ΔgabD | the present invention |
| Plasmids | | |
| pTac15k | pACYC177 derivative, p15A origin, tac promoter, Km$^R$ | 1 |
| pTacxylBC | pTac15k derivative; tac promoter, xylBC from *Caulobacter crescentus*, Km$^R$ | the present invention |
| pTacxylBC_phaAB | pTacxylBC derivative; tac promoter, xylBC from *Caulobacter crescentus*, *R. eutropha* PHA biosynthesis operon promoter, phaAB from *R. eutropha*, Km$^R$ | the present invention |
| pTacxylBC_s4D | pTacxylBC derivative; tac promoter, xylBC from *C. crescentus*, trc promoter sucD, 4hbD from *Clostridium kluyveri*, Km$^R$ | the present invention |
| pPs619C1437Pct540 | pBluescript II KS(+) derivative, *Ralstonia eutropha* PHA biosynthesis operon promoter, *Pseudomonas* sp. MBEL 6-19 phaC$_{Ps6-19}$ variant(phaC1437; E130D, S325T, S477G, Q481K), *Clostridium propionicum* pct$_{Cp}$ variant (pct540; V193A, silent mutations: T78C, T669C, A1125G, T1158C), transcriptional terminator of the *R. eutropha* PHA biosynthesis operon, Ap$^R$ | 2 |
| pPs619C1wtPct540 | pPs619C1437Pct540 derivative, phaC1437 was replaced by phaC1$_{Ps6-19}$ wildtype, Ap$^R$ | 2 |
| pPs619C1202Pct540 | pPs619C1437Pct540 derivative, phaC1437 was replaced by phaC1202 (E130D, Q481K), Ap$^R$ | 2 |
| pPs619C1301Pct540 | pPs619C1437Pct540 derivative, phaC1437 was replaced by phaC1301 (E130D, S325T, Q481K), Ap$^R$ | 2 |
| pPs619C1310Pct540 | pPs619C1437Pct540 derivative, phaC1437 was replaced by phaC1310 (E130D, S477F, Q481K), Ap$^R$ | 2 |
| pPs619C1439Pct540 | pPs619C1437Pct540 derivative, phaC1437 was replaced by phaC1439 (E130D, S325T, S477F, Q481K), Ap$^R$ | 2 |
| pCnCAB | pBluescript II KS(+) derivative, *Ralstonia eutropha* PHA biosynthesis operon promoter, *R. eutropha* phaCAB genes, transcriptional terminator of the *R. eutropha* PHA biosynthesis operon, Ap$^R$ | 3 |

TABLE 1-continued

Strains and plasmids used

| Strains or plasmids | Features[a] | Cited references/sources |
|---|---|---|
| pCnAB | pCnCAB[14] derivative, R. eutropha PHA biosynthesis operon promoter, R. eutropha phaAB, Ap[R] | the present invention |
| ptrc99s4D | trc promoter, sucD, 4hbD from Clostridium kluyveri, Ap[R] | the present invention |

[a]Ap: ampicillin; Km: kanamycin; R: resistance.
[b]Stratagene Cloning System, La Jolla, CA, USA. [c], 1. US 20130078673 A1 2. Yang, T. H. et al. *Appl. Microbiol. Biotechnol.* 90, 603-614 (2011). 3. Yang, T. H. et al. *Biotechnol. Bioeng.* 105, 150-160 (2010).

TABLE 2

Primer sequences used in the present invention

| Cloning | Name (#SEQ ID NO:) | Sequences |
|---|---|---|
| xylBC | xylBC_F (#5) | agacaggaattcatgtcctcagccatctatcccag |
|  | xylBC_R (#6) | agacagctgcagttagacaaggcggacctcatg |
| phaAB | Pcncab_invF (#7) | atgactgacgttgtcatcgtatcc |
|  | Pcncab_invR (#8) | gatttgattgtctctctgccgtc |
|  | phaAB_F (#9) | agacaggcatgccgggcaagtaccttgcc |
|  | phaAB_R (#10) | agacaggcatgctcagcccatatgcaggcc |
| s4D | s4D_F (#11) | agacag gcatgc ttgacaattaatcatccggctc |
|  | s4D_R (#12) | agacag gcatgc ttaatataactttttatatgtgtttactatgtc |
| Knock-out |  |  |
| frdB | frdB_KOF (#13) | gcggaagcagccaataagaaggagaaggcgaatggc tgagatgaaaaaccgacactatagaacgcggccg |
|  | frdB_KOR (#14) | gacgtgtttcgggcagacttcggagcagtagcccac gaaagtacagctccccgcataggccactagtgga |
|  | frdB_EXF (#15) | tgccgccagctaaacgcgtttacggtggcgaagcgg atgcagccgataaggcggaagcagccaataagaa |
|  | frdB_EXR (#16) | aagtctttcgaactttctactttgccctgctgaatg gccgcagccggatcgacgtgtttcgggcagactt |
| poxB | poxB_KOF (#17) | tttctctcccatcccttcccctccgtcagatgaac taaacttgttaccggacactatagaacgcggccg |
|  | poxB_KOR (#18) | gcgcagcatatacaggctgaaacctttggcctgttc gagtttgatctgcgccgcataggccactagtgga |
|  | poxB_EXF (#19) | tatgcccgatgatattcctttcatcgggctatttaa ccgttagtgcctccttctctcccatcccttccc |
|  | poxB_EXR (#20) | tttgttttcgccagttcgatcacttcatcaccgcgt ccgctgatgattgcgcgcagcatatacaggctga |
| adhE | adhE_KOF (#21) | tgaacttaacgcactcgtagagcgtgtaaaaaaagc ccagcgtgaatatggacactatagaacgcggccg |
|  | adhE_KOR (#22) | gctttttctcagctttagccggagcagcttctttc ttcgctgcagtttcccgcataggccactagtgga |
|  | adhE_EXF (#23) | aaaaaagtttaacattatcaggagagcattatggct gttactaatgtcgctgaacttaacgcactcgtagag |
|  | adhE_EXR (#24) | aggggccgtttatgttgccagacagcgctactgatt aagcggattttttcgcttttttctcagctttagccg |
| pflB | pflB_KOF (#25) | taccaaaggtgactggcagaatgaagtaaacgtccg tgacttcattcagagacactatagaacgcggccg |
|  | pflB_KOR (#26) | gcgagttgaaacgtactgcgtagccagatacacgga tggtcagctgcggaccgcataggccactagtgga |
|  | pflB_EXF (#27) | tgttacatgtccgagcttaatgaaaagttagccaca gcctgggaaggttttaccaaaggtgactggcaga |
|  | pflB_EXR (#28) | agattgagtgaaggtacgagtaataacgtcctgctg ctgttcttagtcagcgagttgaaacgtactgcg |
| aceB | aceB_KOF (#29) | ccttcgttcacagtggggaagttttcggatccatga cgaggagctgcacggacactatagaacgcggccg |
|  | aceB_KOR (#30) | aatttgttgtgtacgggttttcatgtgcagatgctc catagtatgtggtggtccgcataggccactagtgga |
|  | aceB_EXF (#31) | cattttaaatgagtagtcttagttgtgctgaacgaa aagagcacaacgatccttcgttcacagtgggga |

TABLE 2-continued

Primer sequences used in the present invention

| Cloning | Name (#SEQ ID NO:) | Sequences |
|---|---|---|
| | aceB_EXR (#32) | aatgccttcccaacgcggttgagtccactctttctg taattcttcaatttgttgtgtacgggttttcatg |
| glcDEFGB | glcDEFGB_KOF (#33) | cagcgcgcaaaaatcagctgccacacaacacaacaa agcgaagcctactcgacactatagaacgcggccg |
| | glcDEFGB_KOR (#34) | cagttactatcatagccccgacaataaaacttgccg gggcttttttgacgctaccgcataggccactagtgg a |
| | glcDEFGB_KOExF (#35) | gctaaagagatagacgaaaacgaaaagcccgcttaa taactgttcacagaagcagcgcgcaaaaatcagc |
| | glcDEFGB_KOExR (#36) | aaaccctgataatcgctccggttatttccgggataa atgtactaccgcagttactatcatagccccgaca |
| ptsG | ptsG_F (#37) | cctgtacacggcgaggctctccccccttgccacgcg tgagaacgtaaaaagacactatagaacgcggccg |
| | ptsG_R (#38) | gtaaaaaggcagccatctggctgccttagtctccc caacgtcttacggaccgcataggccactagtgga |
| | ptsG_exF (#39) | tggcactgaattatttttactctgtgtaataaataaa gggcgcttagatgccctgtacacggcgaggctct |
| | ptsG_exR (#40) | caccgcgtaatttcagcattaccggcacgtatcaat tctgaataacacctgtaaaaaaggcagccatctgg |
| ilvA | ilvA_F (#41) | cggtgcgcgataaatcgaaactgggggggttaataat ggctgactcgcaacgacactatagaacgcggccg |
| | ilvA_R (#42) | gcattttccctaacccgccaaaaagaacctgaacg ccgggttattggttccgcataggccactagtgga |
| | ilvA_exF (#43) | ctttgccctgcgtgcttatgccagcctggcaaccag cgccgacaaaggcgcggtgcgcgataaatcgaaa |
| | ilvA_exR (#44) | cacaaatgacgttgtcgcgcgggtaggcctgataag cgaagcgctatcaggcatttttccctaacccgcc |
| yneI | yneI_F (#45) | gcgtatcttcataccatgactcataaaggagatacc ccgatgaccattacgacactatagaacgcggccg |
| | yneI_R (#46) | accgcaggtctgaaaagacctgcgagtatatcagag ctgaatatgtcgcgccgcataggccactagtgga |
| | yneI_exF (#47) | ttcgtgaataagtggcttaatattattcattttaaa gcaagagtaaatctgcgtatcttcataccatgactc a |
| | yneI_exR (#48) | tgttttctaaaattgcattatccatggcgactgcca ctttctactcctggaccgcaggtctgaaaagacc |
| gabD | gabD_F (#49) | tgccttacacgccgcatttaatcaataaccttgaa aacaggatgtagcggacactatagaacgcggccg |
| | gabD_R (#50) | gactgcggcgctgcattaactcttttattgctgttca ttcgcattctccagccgcataggccactagtgga |
| | gabD_exF (#51) | gcaagccagagtaaccccggacgcacgctgcgagcg gcacgtagtgtggatgccttacacgccgcattta |
| | gabD_exR (#52) | gcgcggtcagcgaaaatcgggtgaatttgcccaacg ccacggggaatcgcctgactgcggcgctgcatta |
| promoter | | |
| ldhA | ldhApc_F (#53) | agaataatcagtaataacagcgcgagaacggcttta tatttacccagcatgacactatagaacgcggccg |
| | ldhApc_R (#54) | ctgttgcaggtacttcttgtcgtactgttttgtgct ataaacggcgagtttcatggtctgtttcctgtgtga a |
| | ldhApc_exF (#55) | cgtgggaacccacagcccgagcgtcatcagcagcgt caacggcacaagaataatcagtaataacagcgcg |
| | ldhApc_exR (#56) | cagcagaaagtcaaaaaattccagctcaaagccaaa ggactcgttcacctgttgcaggtacttcttgtcg |

A metabolite including xylose, glucose, pyruvic acid, acetic acid, formic acid, lactate and succinate was analyzed with an HPLC Varian ProStar 210, USA) equipped with UV/VIS (Varian ProStar 320, USA) and refractive index detectors (Shodex RI-71, Japan) using the MetaCarb 87H column (300×7.8 mm). Cell growth was measured using the Ultraspec 300 spectrophotometer (Amersham Bioscience, Sweden) at a wavelength of 600 nm.

Analysis of intracellular polymer concentration and components was performed using gas chromatography (Agilent 6890N equipped with an Agilent 7683 automatic injector, a flame ionization detector and a fused silica capillary column (ATTM-Wax, 30 m, ID 0.53 mm, film thickness: 1.20 m, Alltech, Deerfield, Ill., USA).

Example 2: Analysis of Production of Glycolate-Containing Polymer in Recombinant *E. coli* Strain Expressing PHA Synthase and Propionyl-CoA Transferase In this Example, genes to be inserted to construct a recombinant *E. coli* strain that produces glycolate-containing PHA were examined.

An enzyme (Pct 540) having a V193A mutation and four silent mutations (T78C, T669C, A1125G and T1158C) in *Clostridium propionicum* propionyl-CoA transferase was selected so that glycolate could be converted to glycolyl-CoA, and the enzyme was identified by measuring its in vitro activity.

Next, for selection of PHA synthase, a test was performed for *Pseudomonas* sp. 6-19-derived PHA synthase (wild-type PhaC1), which produces a poly(lactate-co-3-hydroxybutyrate) having a high content of a lactate fraction, and five mutant enzymes, PhaC1202 (E130D, Q481K), PhaC1301 (E130D, S325T, Q481K), PhaC1310 (E130D, S477F, Q481K), PhaC1437 (E130D, S325T, S477G and Q481K), PhaC1439 (E130D, S325T, S477F, Q481K). To examine the degree to which an intracellular polymer is synthesized from glycolate, sodium glycolate as a precursor was added to medium at a concentration of 2 g/L, and at the same time, 2 g/L of sodium 3-hydroxybutyrate was added in order to promote polymer production by providing 3-hydroxybutyrate-CoA which is a substrate favored by PHA synthase. The results of analysis of polymers produced by the transformed recombinant E. coli XL1-Blue strains are shown in Table 3 below.

TABLE 3

Compositions and concentrations of copolymers produced by recombinant E. coli strains

| Recombinant strains | Polymer compositions[a] (mol %) | | | Polymer concentration (wt %) |
|---|---|---|---|---|
| | LA | GA | 3HB | |
| XL1-Blue/ pPs619CwtPct540 | 0 | 40.1 | 59.9 | 1.9 |
| XL1-Blue/ pPs619C1202Pct540 | 27.0 | 6.9 | 66.1 | 55.0 |
| XL1-Blue/ pPs619C1301Pct540 | 28.9 | 9.6 | 61.5 | 56.7 |
| XL1-Blue/ pPs619C1310Pct540 | 37.2 | 11.0 | 51.8 | 19.7 |
| XL1-Blue/ pPs619C1437Pct540 | 31.6 | 17.2 | 51.2 | 46.6 |
| XL1-Blue/ pPs619C1439Pct540 | 25.6 | 8.2 | 66.2 | 49.4 |

[a]LA: lactate; GA: glycolate; 3HB: 3-hydroxybutyrate.

For mutant enzymes other than wild-type PhaC1 among the above-described genes, it was confirmed that a polymer comprising glycolate and lactate was produced. In the case of the PhaC1437 mutant enzyme, a polymer having the highest contents of glycolate and lactate was produced. Thus, a subsequent experiment was performed using PhaC1437.

Example 3: Production of PLGA Through Metabolic Engineering of E. coli Strain that Uses Xylose as Carbon Source In Example 2, it was confirmed that the E. coli XL1-Blue strain could convert the externally added glycolate into the polymer by PhaC1437 and Pct540 in the cells. Thus, in this Example, metabolic engineering of the E. coli strain was performed in order to produce PLGA directly from a biomass-derived carbon source such as xylose without external addition of glycolate. It was shown that the E. coli XL1-Blue strain had the genes involved in the metabolic pathway that produces glycolate via glyoxylate, but it did not naturally produce glycolate during culture. Thus, enhancement of the glycolate metabolic pathway and optimization of metabolic flux to glycolate were performed.

Regarding a metabolic pathway capable of producing glycolate in E. coli, isocitrate which is a metabolite forming the TCA cycle is converted to glyoxylate (glyoxylate shunt), and then the glyoxylate is converted to glycolate by glyoxylate enzyme. In other words, isocitrate is converted to glyoxylate by isocitrate lyase (glyoxylate shunt) or converted to 2-ketoglutarate by isocitrate dehydrogenase (TCA cycle). This metabolic flux mechanism is regulated by phosphorylation/dephosphorylation of isocitrate dehydrogenase and regulated by various regulators. Preciously, an attempt was made to produce PLGA from glucose by use of this metabolic pathway (U.S. Pat. No. 8,883,463 B2).

In the present invention, an attempt was made to construct an E. coli strain that produces a high concentration of PLGA by using xylose as a main carbon source, in view of the fact that glycolate can be produced from a xylose utilization pathway called the Dahms pathway.

Regarding the Dahms pathway, when a strain such as Caulobacter uses xylose as a carbon source, xylose is converted sequentially into xylonolactone, xylonate, and 2-dehydro-3-deoxy-pentonate which is then separated into glycolaldehyde and pyruvate by aldolase, and the glycolaldehyde is converted into glycolate by aldehyde dehydrogenase (see FIG. 1B). When an E. coli strain uses xylose as a carbon source, xylose enters the cells by a transporter, and then is converted by xylose isomerase and xylulose and metabolized via a pentose phosphate pathway, not the Dahms pathway. Thus, an attempt was made to construct the Dahms pathway in E. coli by introducing external genes from a microorganism that uses the Dahms pathway. Since it is known that enzymes downstream of the Dahms pathway are present in E. coli, xylose dehydrogenase and xylonolactonase which are involved in upstream of the Dahms pathway were amplified from the chromosome of Caulobacter crescentus, thereby constructing a pTacxylBC plasmid. The pTacxylBC vector was transformed into the E. coli XL1-Blue strain which was then cultured in MR medium containing 20 g/l of xylose as a single carbon source, and as a result, 0.89 g/L of glycolate was produced.

Since lactate which is another monomer of PLGA is produced using pyruvate as a precursor, it is important not to reduce to flux to lactate by the conversion of pyruvate to each of acetate and formate. Thus, poxB (pyruvate oxidase) and pflB (pyruvate-formate lyase), which are genes involved in pyruvate conversion, were deleted, and the frdB (fumarate reductase) gene, known to prevent the production of the potential by-product succinate and have the effect of increasing lactate production, was also deleted. In addition, in order to increase a pool of acetyl-CoA functioning to provide Coenzyme A during the conversion of lactate and glycolate into lactyl-CoA and glycol-CoA by Pct540 and in order to prevent the production of ethanol which is a by-product in E. coli fermentation, the adhE gene was also deleted, thereby constructing an X15 strain. The X15 strain constructed as described above produced 1.06 g/L of glycolate (FIG. 3).

In this case, however, lactate was not produced. For this reason, in order to increase lactate production, the existing promoter of the ldhA gene corresponding to lactate dehydrogenase, which is an enzyme that converts pyruvate to lactate, was replaced with a stronger trc promoter, thereby constructing an X15-p strain. As a result, it was confirmed that the amount of lactate produced increased by a very small amount, and up to 0.07 g/l of lactate was produced (FIG. 3). It is believed that maintenance of a stronger lactate flux is important for PLGA production, and an effort was made to prevent the reduction of lactate with time. E. coli has another lactate dehydrogenase-encoding gene (dld) in addition to ldhA. Assuming that the dld gene would convert lactate again to pyruvate, the dld gene was deleted, thereby constructing an X15ld strain. In the case of the constructed X15ld strain, the amount of lactate produced greatly increased to 0.67 g/L and also showed no tendency to decrease with culture time, and at the same time, 0.95 g/L of glycolate was also produced (FIG. 3).

When XylBC, PhaC1437 and Pct540 were all expressed in the X15ld strain, a polymer was produced at a concentration of 3.1 wt % based on the total dry weight of the strain, and a PLGA-like polymer containing lactate and glycolate in amounts of 63.8 mol % and 34.9 mol %, respectively, was produced (Table 4). However, unexpectedly, a polymer containing a very small amount of 2-hydroxybutyrate was produced. To solve this problem, an attempt was made to block the 2-ketobutyrate biosynthesis pathway regarded as a pathway via which 2-hydroxybutyrate could be produced in E. coli. Among two genes (ilvA and tdcB) encoding threonine dehydratase which is an enzyme that converts threonine into 2-ketobutyrate, the activity of ilvA known to play an important role in aerobic culture is inhibited by isoleucine (feedback inhibition). Thus, the recombinant E. coli strain was cultured in medium containing 5 mM of isoleucine, and as a result, it was shown that PLGAs were produced in amounts of 74.5 mol % and 23.7 mol % and a concentration corresponding to 1.9 wt % of the dry weight of the strain) (Table 4).

TABLE 4

Compositions and concentrations of PLGA copolymers produced by recombinant E. coli strain

| Recombinant strains[a] | Polymer compositions[b] (mol %) | | | Polymer concentration |
|---|---|---|---|---|
| | LA | GA | 2HB | (wt %) |
| X15ld | 63.8 | 34.9 | 1.3 | 3.1 |
| X15ld* | 74.5 | 23.7 | 1.8 | 1.9 |

[a]Each strain was transformed with pPs619C1437Pct540 and ptacxylBC and cultured in 100 mM MOPS-containing medium for 96 hours.
[b]LA: lactate; GA: glycolate; 2HB: 2-hydroxybutyrate.
*Cultured in medium supplemented with 5 mM of isoleucine.

Example 4: Development of E. coli Strain that Uses Xylose and Glucose Simultaneously and Evaluation of the Ability to Produce PLGA As mentioned in Example 3 above, the E. coli XL1-Blue strain was transformed with the xylose dehydrogenase-encoding xylB gene and the xylonolactonase-encoding xylC gene and cultured, and as a result, 0.89 g/L of glycolate was produced. In this case, however, the $OD_{600}$ value decreased to about half of that of a control strain, indicating that the cell growth rate and cell density of the strain were low. As a solution to this cell growth inhibition problem, the strain was engineered so that it could also use glucose as an additional carbon source. When E. coli is given xylose and glucose simultaneously, it first uses glucose by a mechanism known as carbon catabolite repression, and then uses xylose as a carbon source after glucose is completely consumed. To overcome this problem and develop a strain that can use the two different carbon sources at the same time, the ptsG gene involved in the glucose transport system was deleted from the E. coli XL1-Blue strain, thereby constructing a XB-p strain. The XB-p strain transformed with pTacxylBC could use glucose and xylose at the same time, and the cell growth level thereof was restored to a level similar to the case in which XylBC was not expressed. In addition, the amount of glycolate produced greatly increased to 1.82 g/L. Thus, it was confirmed that the strategy of introducing glucose as an additional carbon source would be effective. Thus, in Example 4, a strain that uses the two different carbon sources was constructed, thus increasing PLGA production.

Figure 4:
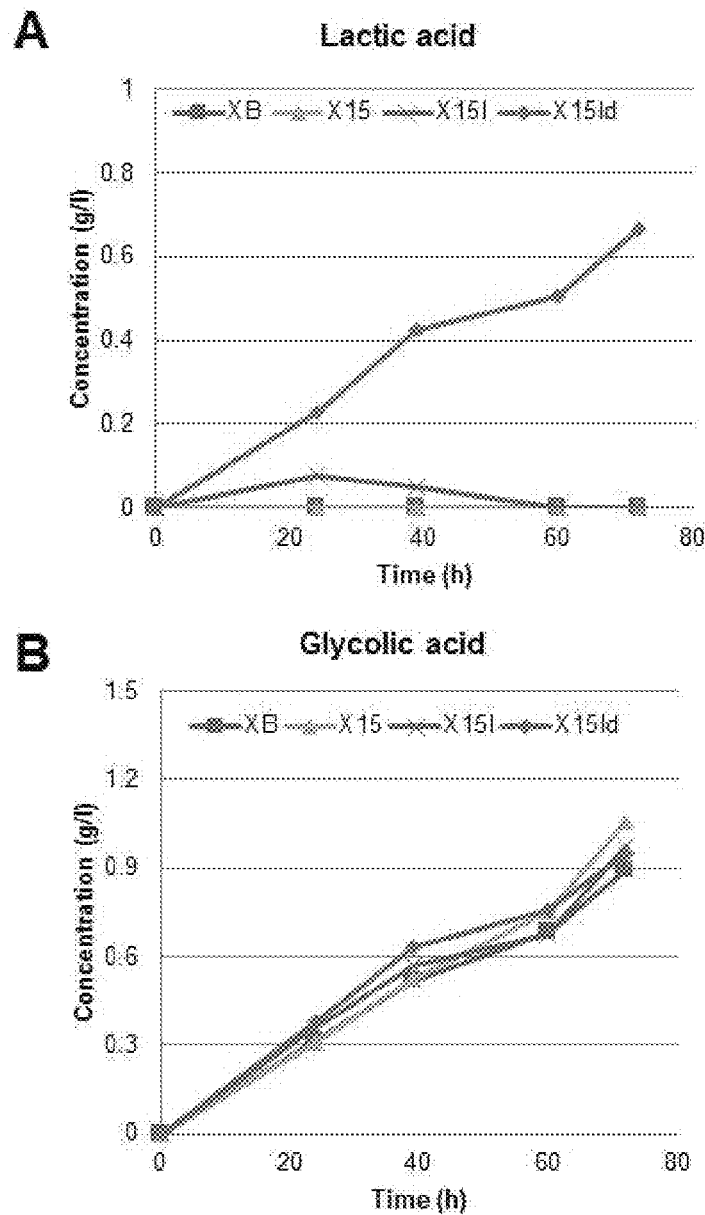
FIGS. 4 and 5 show the lactate and glycolate producing abilities of recombinant E. coli strains constructed in the present invention.

The X15-p strain, obtained by deleting the poxB (pyruvate oxidase), pflB (pyruvate-formate lyase), frdB (fumarate reductase) and adhE genes from the XB-p strain, produced 1.82 g/L of glycolate, and also produced up to 0.99 g/L of lactate, even though lactate production decreased toward to the late stage of culture (FIG. 4).

Although the X15-p strain was cultured while XylBC, PhaC1437 and Pct540 were all expressed, it was confirmed that only negligible amount of a polymer was produced. Glycolate production was maintained above a certain level during culture, while lactate production was up to 0.99 g/l, but decreased again after a certain period of time. Thus, it was believed that enhancement of the flux to lactate would be important for PLGA production (FIG. 4).

Figure 5:
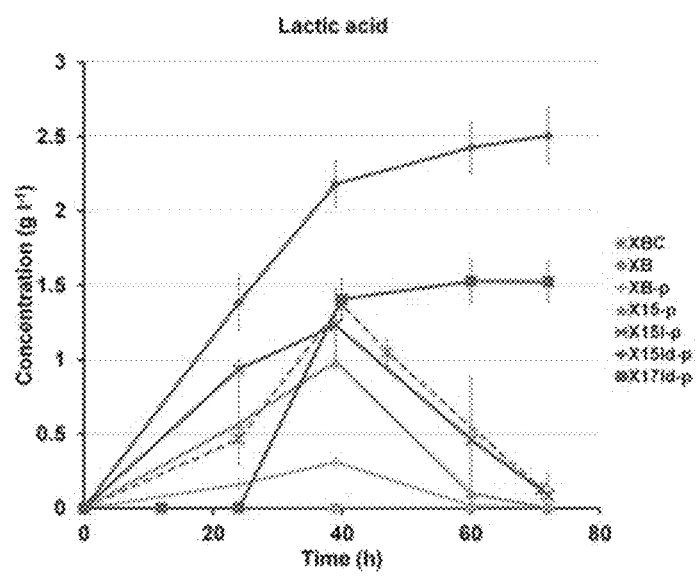
Figure 5:
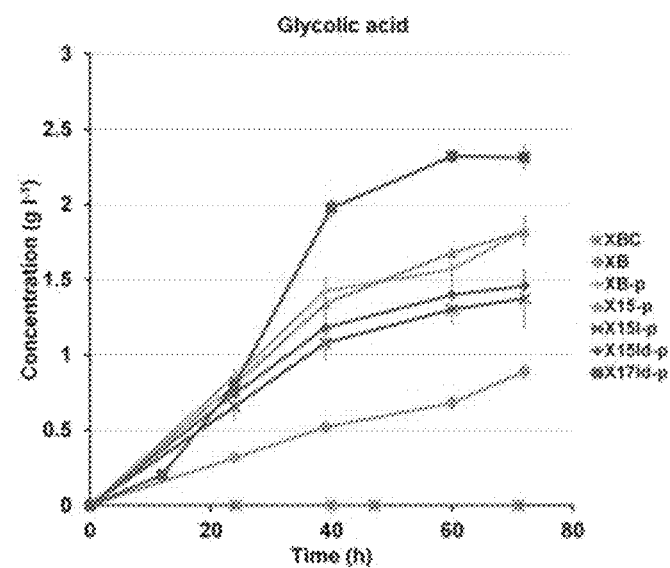

When the X151-p, in which the existing promoter of the ldhA gene corresponding to the gene encoding lactate dehydrogenase that converts pyruvate into lactate was replaced with a stronger trc promoter in order to increase lactate production, was cultured while it expressed XylBC, it was shown that up to 1.38 g/l of lactate was produced and the lactate flux was enhanced (FIG. 5). However, in this strain, like the cased of the previous strain, lactate produced was consumed again after a certain period of time, and there was almost no lactate remaining in the medium at the end of the incubation. However, when XylBC, PhaC1437 and Pct540 were all expressed in the X151-p strain, a polymer comprising lactate and glycolate could be produced. In this case, although lactate production decreased after a certain period of time, like the case of the previous strain, higher lactate production was shown, indicating that the polymer was produced (Table 5).

The case of the X15ld-p strain in which another lactate dehydrogenase-encoding gene (dld) was additionally deleted, lactate production greatly increased to 2.51 g/L, and also showed no tendency to decrease with culture time, and at the same time, glycolate production also increased slightly to 1.48 g/L, indicating that a strain that produces the two compounds while maintaining the compounds at concentrations above certain levels during culture was prepared (FIG. 5).

When XylBC, PhaC1437 and Pct540 were all expressed in the X15ld-p strain, a polymer was produced at a concentration of 16.5 wt % based on the total dry weight of the strain, and a PLGA-like polymer containing lactate and glycolate in amounts of 77.6 mol % and 19.6 mol %, respectively, was produced (Table 5). However, unexpectedly, a polymer containing a very small amount of 2-hydroxybutyrate was produced. To solve this problem, an attempt was made to block the 2-ketobutyrate biosynthesis pathway regarded as a pathway via which 2-hydroxybutyrate could be produced in E. coli. Among two genes (ilvA and tdcB) encoding threonine dehydratase which is an enzyme that converts threonine into 2-ketobutyrate, the ilvA gene known to play an important role in aerobic culture was deleted, thereby constructing an isoleucine-auxotrophic X15ld-pi strain. The X15ld-pi strain expressing all of PhaC1437, Pct540 and XylBC was cultured, and as a result, a PLGA, containing no 2-hydroxybutyrate and comprising 89.6 mol % of lactate and 10.2 mol % of glycolate, could be produced (Table 5).

TABLE 5

Compositions and concentrations of PLGA copolymers produced by recombinant strains

| Recombinant strains[a] | Polymer compositions[b] (mol %) | | | Polymer concentration |
|---|---|---|---|---|
| | LA | GA | 2HB | (wt %) |
| X15l-p | 70.8 | 25.9 | 3.3 | 6.1 |
| X15ld-p | 78.5 | 17.8 | 3.7 | 19.0 |
| X15ld-pi | 88.2 | 11.8 | 0 | 12.6 |

[a]Each strain was transformed with pPs619C1437Pct540 and ptacxylBC and cultured in 100 mM MOPS-containing medium for 96 hours.
[b]LA: lactate; GA: glycolate; 2HB: 2-hydroxybutyrate.

Example 5: Production of PLGA Having High Glycolate Content Through Additional Metabolic Engineering In Example 4, using the recombinant X15l-p and X15ld-p strains engineered from XL1-Blue, PLGA was successfully produced from xylose and glucose, but only polymers having a relatively high lactate content were produced. Thus, in order to increase of the glycolate content of the polymer, engineering for increasing intracellular glycolate production was performed (FIG. 5). To enhance the glyoxylate pathway, the malate synthase-encoding gene aceB, the glycolate oxidase-encoding gene glcDEFG and another glcB gene encoding malate synthase, which form an operon (glcDEFGB), were deleted simultaneously from the chromosomal DNA, thereby constructing a X17ld-p strain. When the X17ld-p strain expressed xylose dehydrogenase and xylonolactonase, it produced glycolate in an amount of 2.32 g/L, which was 1.6 times higher than that by the previous recombinant strain (X15ld-p), indicating that deletion of the genes is effective in increasing glycolate production. When the E. coli X17ld-p strain expressing all of polyhydroxyalkanoate synthase, propionyl-CoA transferase, xylose dehydrogenase and xylonolactonase was cultured, the molar fraction of glycolate greatly increased as can be seen from a change in the production rates of the two monomers, and a PLGA-like polymer having a glycolate content of about 48% was produced at a concentration of about 15.0 wt % (Table 6). In this case, a very small amount of 2-hydroxybutyrate was also contained. For this reason, culture was performed after deletion of the ilvA gene, but cell growth was very inhibited and a sufficient amount of the polymer was not produced. Thus, in another alternative, 5 mM of isoleucine was added to medium in order to inhibit the activity of IlvA without deleting ilvA, followed by culture. As a result, cell growth was not greatly inhibited, a PLGA, containing no 2-hydroxybutyrate and comprising 68.4 mol % of lactate and 31.6 mol % of lactate (the lactate content greatly increased compared to that by the X15ld-pi strain), could be successfully produced (Table 6).

TABLE 6

Compositions and concentrations of PLGA copolymers produced by recombinant strains

| Recombinant strains[a] | Polymer compositions[b] (mol %) | | | Polymer concentration (wt %) |
|---|---|---|---|---|
| | LA | GA | 2HB | |
| X17-ldp | 50.3 | 48.1 | 1.6 | 15.0 |
| X17-ldp* | 68.4 | 31.6 | — | 4.5 |

[a]Each strain was transformed with pPs619C1437Pct540 and ptacxylBC and cultured in 100 mM MOPS-containing medium for 96 hours.
[b]LA: lactate; GA: glycolate; 2HB: 2-hydroxybutyrate.
*The strain was cultured in medium supplemented with 5 mM of isoleucine.

Example 6: Characteristics of PLGA Synthesized in Recombinant E. coli Strain The monomer components of the copolymers synthesized in the present invention were analyzed by gas chromatography and NMR, and the polymers were purified from the cells by an organic solvent extraction method (Jacquel et al., Biochem Eng J 39:15-27, 2008). The molecular weights and thermal properties of the polymers were measured by GPC (gel permeation chromatography) and DSC (differential scanning calorimetry), respectively.

Figure 6:
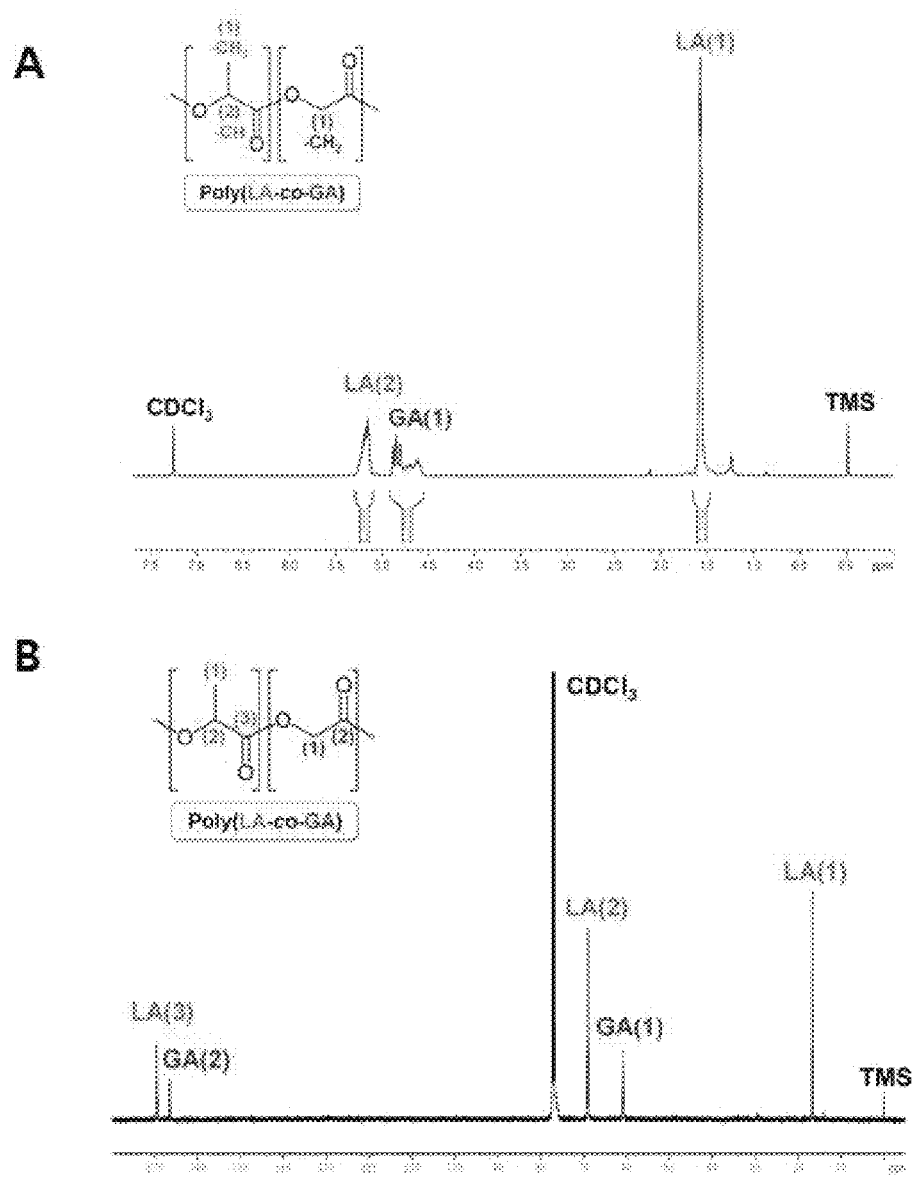
FIG. 6 shows the results of $^1$H NMR and $^{13}$C NMR analysis of a PLGA produced by the recombinant E. coli strain X17ld-p constructed in the present invention.

It was confirmed that the PLGA produced by the E. coli X17ld-p was comprised of 50.3 mol % lactate and 48.1 mol % glycolate, and had the same structure as that of chemically synthesized PLGA, as analyzed by $^1$H NMR and $^{13}$C NMR (FIG. 5). In the 600 MHz $^1$H NMR spectrum of the PLGA, the oxymethine proton (—OCH—) of lactate could be seen at 5.2 ppm, and the methyl proton (—CH$_3$) of glycolate could be seen at a peak of 4.6-4.9 ppm (FIG. 6A). In the 125 MHz $^{13}$C NMR spectrum of the PLGA, the carbonyl carbon peak of GA*-GA sequence appeared at 169.4 ppm, and the carbonyl peak of LA*-LA and LA-LA* sequences appeared at 169.63 ppm, and the carbonyl peak of LA*-GA+GA-LA'sequences appeared at 169.80 ppm (FIG. 6B).

The molecular weight values obtained by GPC analysis and the thermal property values obtained by DSC analysis are shown in Table 5. The molecular weight was in the range of 15 kDa to 25 kDa, which corresponds to the molecular weight of PLGA which is frequently used in drug delivery, and a peak corresponding to the melting point (Tm) was not observed in the DSC graph, indicating that the same amorphous PLGA as a PLGA produced by chemical synthesis was produced. In addition, the glass transition temperature (Tg) was in the range of 40° C. to 46° C., which was equal to that of a commercially available PLGA containing a very small amount of 2-HB (Table 7).

TABLE 7

Molecular weights and thermal properties of PLGA copolymers produced by recombinant E. coli strains

| Recombinant strains[a] | Polymer compositions[b] (mol %) | | | Molecular weights (Da) | | | Tg(° C.) |
|---|---|---|---|---|---|---|---|
| | LA | GA | 2HB | Mn | Mw | Mw/Mn | |
| X15l-p | 70.8 | 25.9 | 3.3 | 10115 | 15493 | 1.53 | 40.3 |
| X15ld-p | 78.5 | 17.8 | 3.7 | 15270 | 25375 | 1.66 | 45.3 |
| X17ld-p | 50.3 | 48.1 | 1.6 | 6648 | 19125 | 2.88 | 42.3 |
| X15ld-pi | 88.2 | 11.8 | 0 | 15595 | 24446 | 1.57 | 46.0 |
| X17ld-p* | 68.4 | 31.6 | 0 | 9935 | 18026 | 1.81 | 44.1 |

[a]Each strain was transformed with pPs619C1437Pct540 and ptacxylBC and cultured in 100 mM MOPS-containing medium for 96 hours.
[b]LA: lactate; GA: glycolate; 2HB: 2-hydroxybutyrate.
*The strain was cultured in medium supplemented with 5 mM of isoleucine.

Example 7: Construction of Recombinant Microbial Strain that Produces Poly(Lactate-Co-Glycolate-Co-3-Hydrobutyrate)

Figure 7:
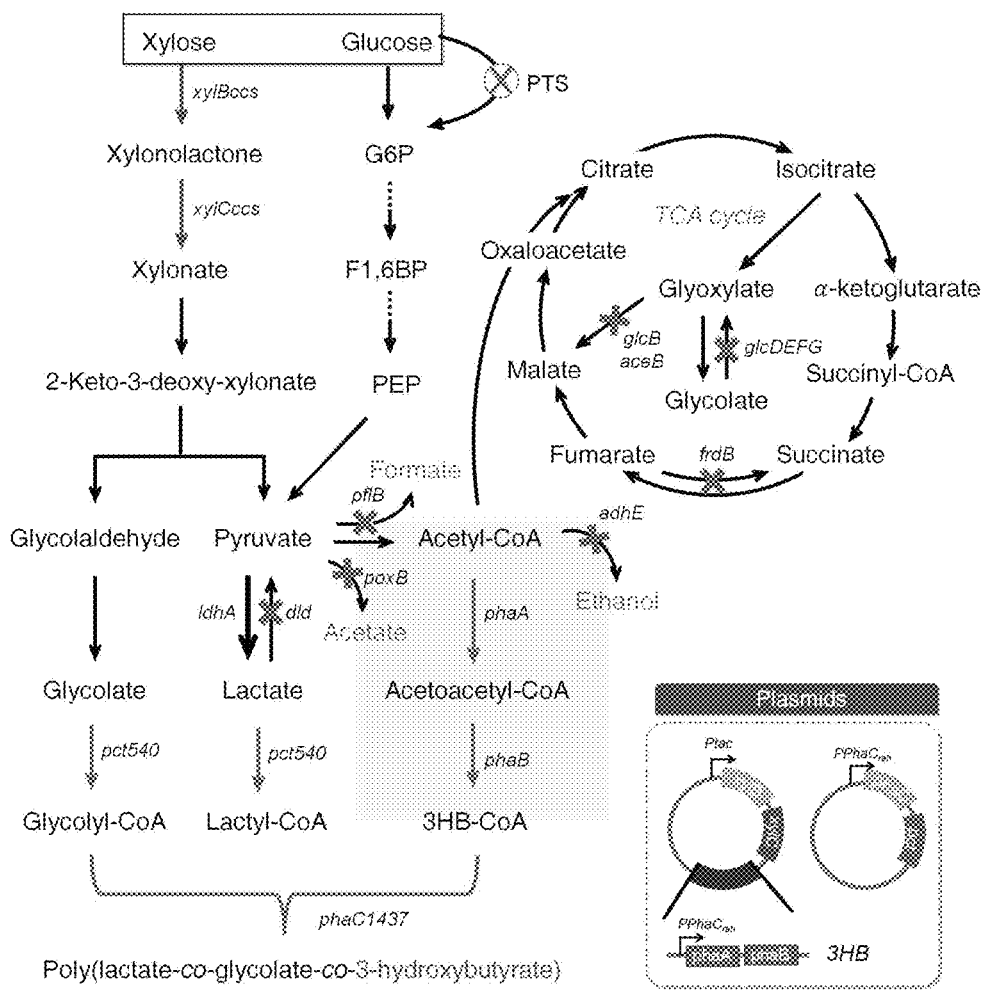
FIG. 7 shows a poly(lactate-co-glycolate-co-3-hydroxybutyrate) production pathway provided by metabolic engineering performed in the present invention.

3-hydroxybutyrate is the most well-known monomer of PHA, and a metabolic pathway for biosynthesis of poly-3-hydroxybutyrate was introduced in order to develop a microbial strain that produces a polymer comprising lactate, glycolate and 3-hydroxybutyrate (FIG. 7). The pTacxylB-C_phaAB plasmid (Table 1), obtained by cloning the beta-ketothiolase-encoding gene phaA and acetoacetyl-CoA reductase-encoding gene phaB from R. eutropha, and the pPs619C1437Pct540 plasmid was transformed into each of the X15ld-p and X17ld-p strains. The strains were cultured in 100 mM MOPS-containing MR medium supplemented with 5 mM isoleucine for 96 hours. As a result, the recombinant E. coli X15ld-p strain produced poly(51.9 mol % lactate-co-7.3 mol % glycolate-co-40.8 mol % 3-hydroxybutyrate) at a concentration of 29.5 wt %, and the X17ld-p strain produced poly(63.3 mol % lactate-co-13.2 mol % glycolate-co-23.5 mol % 3-hydroxybutyrate) at a concentration of 20.0 wt %.

Example 8: Construction of Recombinant Microbial Strain that Produces Poly(Lactate-Co-Glycolate-Co-4-Hydroxybutyrate)

Figure 8:
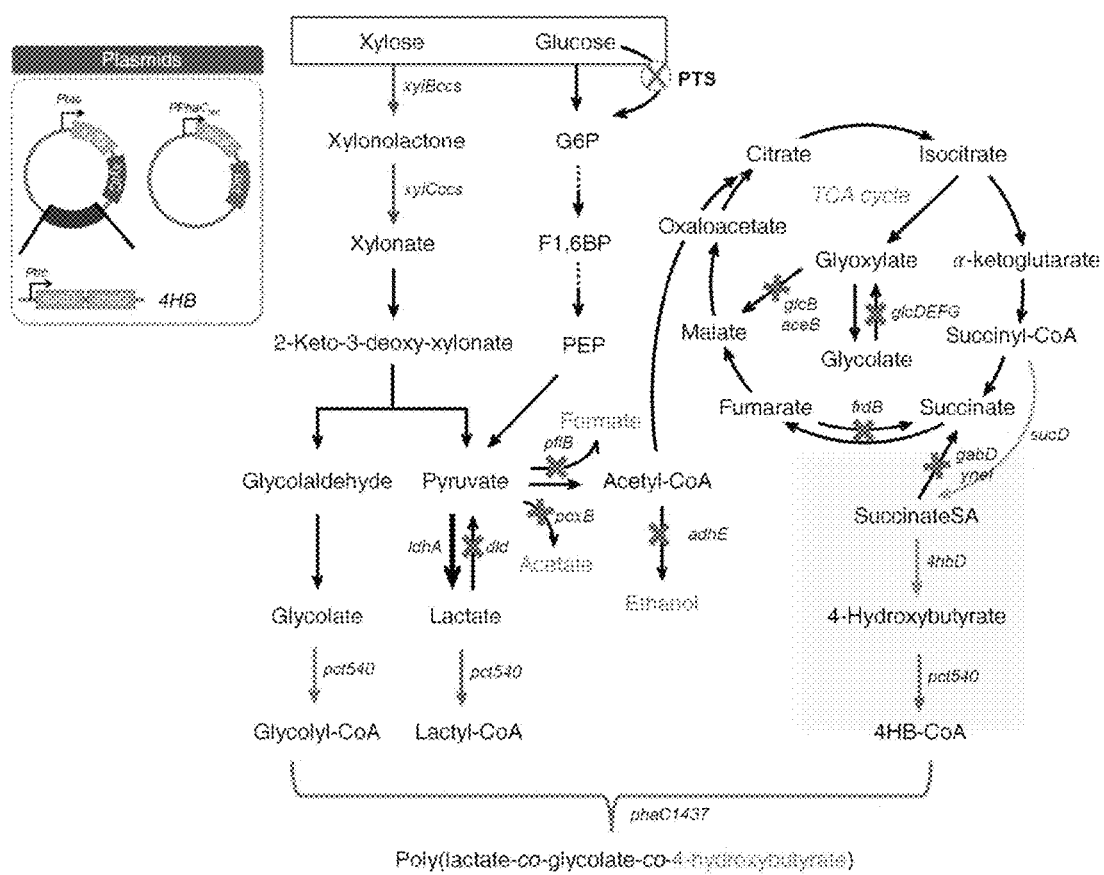
FIG. 8 shows a poly(lactate-co-glycolate-co-4-hydroxybutyrate) production pathway provided by metabolic engineering performed in the present invention.

In order to produce 4-hydroxybutyrate without supplying an external precursor, the CoA-dependent succinate semialdehyde dehydrogenase-encoding gene sucD and the 4-hydroxybutyrate dehydrogenase-encoding gene 4hbD were amplified from the chromosome of *Clostridium kluyveri*, thereby constructing a pTacxylBC_s4D plasmid (Table 1). When the recombinant *E. coli* X17ld-p strain transformed with the pTacxylBC_s4D plasmid and the pPs619C1437Pct540 plasmid was cultured in MR medium supplemented with 5 mM isoleucine and 100 mM MOPS while 10 g/L of xylose and 10 g/L of glucose as carbon sources were supplied to the medium, it produced poly(61.2 mol % lactate-co-38.4 mol % glycolate-co-0.4 mol % 4-hydroxybutyrate) at a concentration of 7.3 wt % for 96 hours of culture. In order to increase the 4-hydroxybutyrate fraction, two genes (yneI and gabD) encoding succinate semialdehyde dehydrogenase, which converts succinate semialdehyde into succinate and is in competition with 4Hbd, were deleted from the X17ld-p strain, thereby constructing an X17ld-pyg strain (Table 1 and FIG. 8). The X17ld-pyg strain expressing all of PhaC1437, Pct540, XylBC, SucD and 4HbD was cultured under the above-described conditions, and as a result, poly(67.1 mol % lactate-co-23.8 mol % glycolate-co-9.1 mol % 4-hydroxybutyrate) was produced at a concentration of 13.8 wt %. In this case, the content of 4-hydroxybutyrate greatly increased to 9.1 mol %, indicating that deletion of the two genes (yneI and gabD) is effective for increasing the 4-hydroxybutyrate flux.

Example 9: Production of Various Copolymers Comprising Lactate and Glycolate by Use of PLGA-Producing Recombinant Microbial Strain In order to produce copolymers containing various hydroxycarboxylic acids, in addition to the copolymers containing 3-hydroxybutyrate and 4-hydroxybutyrate, produced in Examples 7 and 8, 2-hydroxyisovalerate, 5-hydroxyvalerate and 6-hydroxyhexanoate were selected.

When the recombinant *E. coli* X17ld-p strain transformed with the pTacxylBC and pPs619C1437Pct540 plasmids was cultured in 5 mM isoleucine-containing medium after adding 2 g/L of 2-hydroxyisovalerate as a precursor, it produced poly(53.6 mol % lactate-co-23.3 mol % glycolate-co-23.1 mol % 2-hydroxyisovalerate) at a concentration of 20.8 wt %.

The recombinant strain was cultured after adding 2 g/L of sodium 5-hydroxyvalerate as a precursor, and as a result, poly(69.2 mol % lactate-co-24.7 mol % glycolate-co-6.1 mol % 5-hydroxyvalerate) was produced at a concentration of 16.7 wt %. In addition, when the strain was cultured after adding 2 g/L of 6-hydroxyhexanoate as a precursor, it produced poly(76.4 mol % lactate-co-22.0 mol % glycolate-co-1.6 mol % 6-hydroxyhexanoate) at a concentration of 16.5 wt %.

INDUSTRIAL APPLICABILITY

According to the present invention, it is possible to produce poly(lactate-co-glycolate) and its copolymers at high concentrations without having to supply lactate and glycolate precursors from external sources.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A recombinant microorganism having the ability to produce poly(lactate-co-glycolate), wherein a polyhydroxyalkanoate synthase-encoding gene, a propionyl-CoA transferase-encoding gene, a xylose dehydrogenase-encoding gene, and a xylonolactonase-encoding gene are introduced in a microorganism having the ability to produce lactate from pyruvic acid, wherein the recombinant microorganism has an ability to produce poly(lactate-co-glycolate) without supplying glycolate.

2. The recombinant microorganism of claim 1, wherein the polyhydroxyalkanoate synthase is PHA synthase derived from *Pseudomonas* sp. 6-19 or a mutant enzyme of PHA synthase, which has an amino acid sequence selected from the following amino acid sequences:
   an amino acid sequence comprising at least one mutation selected from the group consisting of E130D, S325T, S477G, S477F, S477Y, S477G and Q481K in the amino acid sequence of SEQ ID NO: 1;
   an amino acid sequence (PhaC1202) comprising mutations of E130D and Q481K in the amino acid sequence of SEQ ID NO: 1;
   an amino acid sequence (PhaC1301) comprising mutations of E130D, S325T and Q481K in the amino acid sequence of SEQ ID NO: 1;
   an amino acid sequence (PhaC1310) comprising mutations of E130D, S477F and Q481K in the amino acid sequence of SEQ ID NO: 1;
   an amino acid sequence (PhaC1437) comprising mutations of E130D, S325T, S477G and Q481K in the amino acid sequence of SEQ ID NO: 1; and
   an amino acid sequence (PhaC1439) comprising mutations of E130D, S325T, S477F and Q481K in the amino acid sequence of SEQ ID NO: 1.

3. The recombinant microorganism of claim 1, wherein the propionyl-CoA transferase is a Pct540 enzyme having the amino acid sequence of SEQ ID NO: 2.

4. The recombinant microorganism of claim 1, wherein the chromosomal promoter of a lactate dehydrogenase-encoding gene is replaced with a strong promoter selected from the group consisting of trc, tac, pBAD, trp, lacUV5, and T7.

5. The recombinant microorganism of claim 1, wherein one or more genes selected from the group consisting of a glucose PTS enzyme IIBC component-encoding gene, an aldehyde-alcohol dehydrogenase-encoding gene, a pyruvate-formate lyase-encoding gene, a fumarate reductase-encoding gene, a pyruvate oxidase-encoding gene, a did gene that is a lactate dehydrogenase-encoding gene, a malate synthase-encoding gene, and a glycolate oxidase-encoding gene is deleted from the recombinant microorganism.

6. The recombinant microorganism of claim 1, wherein a beta-ketothiolase-encoding gene and an acetoacetyl-CoA reductase-encoding gene are further introduced in the microorganism, and the recombinant microorganism has the ability to produce poly(lactate-co-glycolate-co-3-hydroxybutyrate).

7. The recombinant microorganism of claim 6, wherein one or more genes selected from the group consisting of a glucose PTS enzyme IIBC component-encoding gene, an aldehyde-alcohol dehydrogenase-encoding gene, a pyruvate-formate lyase-encoding gene, a fumarate reductase-encoding gene, a pyruvate oxidase-encoding gene, a did gene that is a lactate dehydrogenase-encoding gene, a malate synthase-encoding gene, and a glycolate oxidase-encoding gene is further deleted from the recombinant microorganism.

8. The recombinant microorganism of claim 1, wherein a CoA-dependent succinate semialdehyde dehydrogenase-encoding gene, and a 4-hydroxybutyrate dehydrogenase-encoding gene are further introduced in the microorganism, and the recombinant microorganism has the ability to produce poly(lactate-co-glycolate-co-4-hydroxybutyrate).

9. The recombinant microorganism of claim 8, wherein a glucose PTS enzyme IIBC component-encoding gene, an aldehyde-alcohol dehydrogenase-encoding gene, a pyruvate-formate lyase-encoding gene, a fumarate reductase-encoding gene, a pyruvate oxidase-encoding gene, a did gene that is a lactate dehydrogenase-encoding gene, a malate synthase-encoding gene, and a glycolate oxidase-encoding gene are further deleted from the recombinant microorganism.

10. A method for producing poly(lactate-co-glycolate), comprising the steps of:
(a) producing poly(lactate-co-glycolate) by culturing the recombinant microorganism having the ability to produce poly(lactate-co-glycolate) of claim 1 without supplying glycolate; and
(b) recovering the produced poly(lactate-co-glycolate).

11. A method for producing poly(lactate-co-glycolate-co-3-hydroxybutyrate) comprising the steps of:
(a) producing poly(lactate-co-glycolate-co-3-hydroxybutyrate) by culturing the recombinant microorganism having the ability to produce poly(lactate-co-glycolate-co-3-hydroxybutyrate) of claim 6 without supplying glycolate; and
(b) recovering the produced poly(lactate-co-glycolate-co-3-hydroxybutyrate).

12. A method for producing poly(lactate-co-glycolate-co-4-hydroxybutyrate) comprising the steps of:
(a) producing poly(lactate-co-glycolate-co-4-hydroxybutyrate) by culturing the recombinant microorganism having the ability to produce poly(lactate-co-glycolate-co-4-hydroxybutyrate) of claim 8 without supplying glycolate; and
(b) recovering the produced poly(lactate-co-glycolate-co-4-hydroxybutyrate).

13. A method for producing poly(lactate-co-glycolate-co-hydroxycarboxylic acid) comprising the steps of:
(a) producing poly(lactate-co-glycolate-co-hydroxycarboxylic acid) by culturing the recombinant microorganism of claim 1 without supplying glycolate in the presence of hydroxycarboxylic acid; and
(b) recovering the produced poly(lactate-co-glycolate-co-hydroxycarboxylic acid).

14. The method of claim 13, wherein the hydroxycarboxylic acid is selected from the group consisting of 2-hydroxyisovalerate, 5-hydroxyvalerate, and 6-hydroxyhexanoate.

* * * * *

UNITED STATES PATENT AND TRADEMARK OFFICE
CERTIFICATE OF CORRECTION

PATENT NO. : 10,640,774 B2
APPLICATION NO. : 16/071680
DATED : May 5, 2020
INVENTOR(S) : Sang Yup Lee et al.

Page 1 of 1

It is certified that error appears in the above-identified patent and that said Letters Patent is hereby corrected as shown below:

In the Claims

Column 50, Line 32: "did" should be -- dld --.

Column 50, Line 48: "did" should be -- dld --.

Column 50, Line 63: "did" should be -- dld --.

Signed and Sealed this
Ninth Day of June, 2020

Andrei Iancu
*Director of the United States Patent and Trademark Office*